US010561426B1

(12) United States Patent
Dayton et al.

(10) Patent No.: US 10,561,426 B1
(45) Date of Patent: Feb. 18, 2020

(54) BONE CUTTING GUIDE SYSTEMS AND METHODS

(71) Applicant: Treace Medical Concepts, Inc., Ponte Vedra, FL (US)

(72) Inventors: Paul Dayton, Fort Dodge, IA (US); Robert D. Santrock, Morgantown, WV (US); Daniel J. Hatch, Greeley, CO (US); W. Bret Smith, Lexington, SC (US); Carlos Eduardo Gil, Jacksonville Beach, FL (US); Sean F. Scanlan, Jacksonville, FL (US); Joe William Ferguson, Ponte Vedra Beach, FL (US); F. Barry Bays, Collierville, TN (US); John T. Treace, Ponte Vedra Beach, FL (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 0 days.

(21) Appl. No.: 16/593,153

(22) Filed: Oct. 4, 2019

Related U.S. Application Data

(63) Continuation of application No. 15/603,056, filed on May 23, 2017, which is a continuation of application No. 14/990,574, filed on Jan. 7, 2016, now Pat. No. 9,687,250.

(60) Provisional application No. 62/100,641, filed on Jan. 7, 2015.

(51) Int. Cl.
*A61B 17/15* (2006.01)

(52) U.S. Cl.
CPC ............ *A61B 17/151* (2013.01); *A61B 17/15* (2013.01)

(58) Field of Classification Search
CPC ............................. A61B 17/15; A61B 17/151
See application file for complete search history.

(56) References Cited

U.S. PATENT DOCUMENTS

| 4,069,824 | A | 1/1978 | Weinstock |
| 4,159,716 | A | 7/1979 | Borchers |
| 4,187,840 | A | 2/1980 | Watanabe |
| 4,335,715 | A | 6/1982 | Kirkley |

(Continued)

FOREIGN PATENT DOCUMENTS

| AU | 2009227957 B2 | 7/2014 |
| CA | 2491824 A1 | 9/2005 |

(Continued)

OTHER PUBLICATIONS

Rx-Fix Mini Rail External Fixator, Wright Medical Technology, Brochure, Aug. 15, 2014, 2 pages.

(Continued)

*Primary Examiner* — Andrew Yang
(74) *Attorney, Agent, or Firm* — Fredrikson & Byron, P.A.

(57) ABSTRACT

A bone cutting guide may include a support that contains a shaft movable relative to the support. The shaft may carry a guide member having one or more cut guides through which a clinician inserts a cutting member to cut bone positioned under the guide cut guides. In operation, a clinician may fixate the support of the bone cutting guide to a bone and translate the guide member until the one or more cut guides are positioned at a desired cut location. The clinician may then perform a cut through the cut guide. In some examples, the bone cutting guide includes additional components, such as bridging member or secondary cut guide, to provide additional functionality.

20 Claims, 18 Drawing Sheets

(56) References Cited

U.S. PATENT DOCUMENTS

| | | | |
|---|---|---|---|
| 4,338,927 A | 7/1982 | Volkov et al. |
| 4,349,018 A | 9/1982 | Chambers |
| 4,409,973 A | 10/1983 | Neufeld |
| 4,440,168 A | 4/1984 | Warren |
| 4,501,268 A | 2/1985 | Comparetto |
| 4,502,474 A | 3/1985 | Comparetto |
| 4,509,511 A | 4/1985 | Neufeld |
| 4,565,191 A | 1/1986 | Slocum |
| 4,570,624 A | 2/1986 | Wu |
| 4,627,425 A | 12/1986 | Reese |
| 4,628,919 A | 12/1986 | Clyburn |
| 4,632,102 A | 12/1986 | Comparetto |
| 4,664,102 A | 5/1987 | Comparetto |
| 4,708,133 A | 11/1987 | Comparetto |
| 4,750,481 A | 6/1988 | Reese |
| 4,757,810 A | 7/1988 | Reese |
| 4,895,141 A | 1/1990 | Koeneman et al. |
| 4,952,214 A | 8/1990 | Comparetto |
| 4,978,347 A | 12/1990 | Ilizarov |
| 4,988,349 A | 1/1991 | Pennig |
| 4,995,875 A | 2/1991 | Coes |
| 5,021,056 A | 6/1991 | Hofmann et al. |
| 5,035,698 A | 7/1991 | Comparetto |
| 5,042,983 A | 8/1991 | Rayhack |
| 5,049,149 A | 9/1991 | Schmidt |
| 5,053,039 A | 10/1991 | Hofmann et al. |
| 5,078,719 A | 1/1992 | Schreiber |
| 5,112,334 A | 5/1992 | Alchermes et al. |
| 5,147,364 A | 9/1992 | Comparetto |
| 5,176,685 A | 1/1993 | Rayhack |
| 5,207,676 A | 5/1993 | Canadell et al. |
| 5,246,444 A | 9/1993 | Schreiber |
| 5,254,119 A | 10/1993 | Schreiber |
| 5,312,412 A | 5/1994 | Whipple |
| 5,358,504 A | 10/1994 | Paley et al. |
| 5,364,402 A | 11/1994 | Mumme et al. |
| 5,413,579 A | 5/1995 | Du Toit |
| 5,417,694 A | 5/1995 | Marik et al. |
| 5,449,360 A | 9/1995 | Schreiber |
| 5,470,335 A | 11/1995 | Du Toit |
| 5,490,854 A | 2/1996 | Fisher et al. |
| 5,529,075 A | 6/1996 | Clark |
| 5,540,695 A | 7/1996 | Levy |
| 5,578,038 A | 11/1996 | Slocum |
| 5,601,565 A | 2/1997 | Huebner |
| 5,613,969 A | 3/1997 | Jenkins, Jr. |
| 5,620,442 A | 4/1997 | Bailey et al. |
| 5,620,448 A | 4/1997 | Puddu |
| 5,643,270 A | 7/1997 | Combs |
| 5,667,510 A | 9/1997 | Combs |
| H1706 H | 1/1998 | Mason |
| 5,722,978 A | 3/1998 | Jenkins |
| 5,749,875 A | 5/1998 | Puddu |
| 5,779,709 A | 7/1998 | Harris et al. |
| 5,788,695 A | 8/1998 | Richardson |
| 5,803,924 A | 9/1998 | Oni et al. |
| 5,810,822 A | 9/1998 | Mortier |
| 5,843,085 A | 12/1998 | Graser |
| 5,893,553 A | 4/1999 | Pinkous |
| 5,911,724 A | 6/1999 | Wehrli |
| 5,935,128 A | 8/1999 | Carter et al. |
| 5,941,877 A | 8/1999 | Viegas et al. |
| 5,951,556 A | 9/1999 | Faccioli et al. |
| 5,980,526 A | 11/1999 | Johnson et al. |
| 5,984,931 A | 11/1999 | Greenfield |
| 6,007,535 A | 12/1999 | Rayhack et al. |
| 6,027,504 A | 2/2000 | McGuire |
| 6,030,391 A | 2/2000 | Brainard et al. |
| 6,162,223 A | 12/2000 | Orsak et al. |
| 6,171,309 B1 | 1/2001 | Huebner |
| 6,203,545 B1 | 3/2001 | Stoffella |
| 6,248,109 B1 | 6/2001 | Stoffella |
| 6,391,031 B1 | 5/2002 | Toomey |
| 6,478,799 B1 | 11/2002 | Williamson |
| 6,511,481 B2 | 1/2003 | von Hoffmann et al. |
| 6,547,793 B1 | 4/2003 | McGuire |
| 6,676,662 B1 | 1/2004 | Bagga et al. |
| 6,719,773 B1 | 4/2004 | Boucher et al. |
| 6,743,233 B1 | 6/2004 | Baldwin et al. |
| 6,755,838 B2 | 6/2004 | Trnka |
| 6,796,986 B2 | 9/2004 | Duffner |
| 6,859,661 B2 | 2/2005 | Tuke |
| 7,018,383 B2 | 3/2006 | McGuire |
| 7,033,361 B2 | 4/2006 | Collazo |
| 7,112,204 B2 | 9/2006 | Justin et al. |
| 7,182,766 B1 | 2/2007 | Mogul |
| 7,241,298 B2 | 7/2007 | Nemec et al. |
| 7,282,054 B2 | 10/2007 | Steffensmeier et al. |
| 7,377,924 B2 | 5/2008 | Raistrick et al. |
| 7,465,303 B2 | 12/2008 | Riccione et al. |
| 7,540,874 B2 | 6/2009 | Trumble et al. |
| 7,572,258 B2 | 8/2009 | Stiernborg |
| 7,641,660 B2 | 1/2010 | Lakin et al. |
| D610,257 S | 2/2010 | Horton |
| 7,686,811 B2 | 3/2010 | Byrd et al. |
| 7,691,108 B2 | 4/2010 | Lavallee |
| 7,763,026 B2 | 7/2010 | Egger et al. |
| D629,900 S | 12/2010 | Fisher |
| 7,967,823 B2 | 6/2011 | Ammann et al. |
| 7,972,338 B2 | 7/2011 | O'Brien |
| D646,389 S | 10/2011 | Claypool et al. |
| 8,057,478 B2 | 11/2011 | Kuczynski et al. |
| 8,062,301 B2 | 11/2011 | Ammann et al. |
| D651,315 S | 12/2011 | Bertoni et al. |
| D651,316 S | 12/2011 | May et al. |
| 8,080,010 B2 | 12/2011 | Schulz et al. |
| 8,083,746 B2 | 12/2011 | Novak |
| 8,123,753 B2 | 2/2012 | Poncet |
| 8,137,406 B2 | 3/2012 | Novak et al. |
| 8,147,530 B2 | 4/2012 | Strnad et al. |
| 8,167,918 B2 | 5/2012 | Strnad et al. |
| 8,172,848 B2 | 5/2012 | Tomko et al. |
| 8,192,441 B2 | 6/2012 | Collazo |
| 8,197,487 B2 | 6/2012 | Poncet et al. |
| 8,231,623 B1 | 7/2012 | Jordan |
| 8,231,663 B2 | 7/2012 | Kay et al. |
| 8,236,000 B2 | 8/2012 | Ammann et al. |
| 8,246,561 B1 | 8/2012 | Agee et al. |
| D666,721 S | 9/2012 | Wright et al. |
| 8,262,664 B2 | 9/2012 | Justin et al. |
| 8,277,459 B2 | 10/2012 | Sand et al. |
| 8,282,644 B2 | 10/2012 | Edwards |
| 8,282,645 B2 | 10/2012 | Lawrence et al. |
| 8,292,966 B2 | 10/2012 | Morton |
| 8,303,596 B2 | 11/2012 | Plassky et al. |
| 8,313,492 B2 | 11/2012 | Wong et al. |
| 8,323,289 B2 | 12/2012 | Re |
| 8,337,503 B2 | 12/2012 | Lian |
| 8,343,159 B2 | 1/2013 | Bennett |
| 8,377,105 B2 | 2/2013 | Buescher |
| D679,395 S | 4/2013 | Wright et al. |
| 8,409,209 B2 | 4/2013 | Ammann et al. |
| 8,435,246 B2 | 5/2013 | Fisher et al. |
| 8,475,462 B2 | 7/2013 | Thomas et al. |
| 8,496,662 B2 | 7/2013 | Novak et al. |
| 8,523,870 B2 | 9/2013 | Green, II et al. |
| 8,529,571 B2 | 9/2013 | Horan et al. |
| 8,540,777 B2 | 9/2013 | Ammann et al. |
| D694,884 S | 12/2013 | Mooradian et al. |
| D695,402 S | 12/2013 | Dacosta et al. |
| 8,652,142 B2 | 2/2014 | Geissler |
| 8,657,820 B2 | 2/2014 | Kubiak et al. |
| D701,303 S | 3/2014 | Cook |
| 8,672,945 B2 | 3/2014 | Lavallee et al. |
| 8,696,716 B2 | 4/2014 | Kartalian et al. |
| 8,702,715 B2 | 4/2014 | Ammann et al. |
| D705,929 S | 5/2014 | Frey |
| 8,715,363 B2 | 5/2014 | Ratron et al. |
| 8,728,084 B2 | 5/2014 | Berelsman et al. |
| 8,758,354 B2 | 6/2014 | Habegger et al. |
| 8,764,760 B2 | 7/2014 | Metzger et al. |
| 8,764,763 B2 | 7/2014 | Wong et al. |
| 8,771,279 B2 | 7/2014 | Philippon et al. |
| 8,777,948 B2 | 7/2014 | Bernsteiner |

(56) References Cited

U.S. PATENT DOCUMENTS

| | | |
|---|---|---|
| 8,784,427 B2 | 7/2014 | Fallin et al. |
| 8,784,457 B2 | 7/2014 | Graham |
| 8,795,286 B2 | 8/2014 | Sand et al. |
| 8,801,727 B2 | 8/2014 | Chan et al. |
| 8,808,303 B2 | 8/2014 | Stemniski et al. |
| 8,828,012 B2 | 9/2014 | May et al. |
| 8,858,602 B2 | 10/2014 | Weiner et al. |
| 8,882,778 B2 | 11/2014 | Ranft |
| 8,882,816 B2 | 11/2014 | Kartalian et al. |
| 8,888,785 B2 | 11/2014 | Ammann et al. |
| D720,456 S | 12/2014 | Dacosta et al. |
| 8,900,247 B2 | 12/2014 | Tseng et al. |
| 8,906,026 B2 | 12/2014 | Ammann et al. |
| 8,945,132 B2 | 2/2015 | Plassky et al. |
| 8,998,903 B2 | 4/2015 | Price et al. |
| 8,998,904 B2 | 4/2015 | Zeetser et al. |
| 9,023,052 B2 | 5/2015 | Lietz et al. |
| 9,044,250 B2 | 6/2015 | Olsen et al. |
| 9,060,822 B2 | 6/2015 | Lewis et al. |
| 9,089,376 B2 | 7/2015 | Medoff et al. |
| 9,101,421 B2 | 8/2015 | Blacklidge |
| 9,107,715 B2 | 8/2015 | Blitz et al. |
| 9,113,920 B2 | 8/2015 | Ammann et al. |
| D740,424 S | 10/2015 | Dacosta et al. |
| D765,844 S | 9/2016 | DaCosta |
| D766,434 S | 9/2016 | DaCosta |
| D766,437 S | 9/2016 | DaCosta |
| D766,438 S | 9/2016 | DaCosta |
| D766,439 S | 9/2016 | DaCosta |
| 9,750,538 B2 | 9/2017 | Soffiatti et al. |
| 9,785,747 B2 | 10/2017 | Geebelen |
| 10,028,750 B2 | 7/2018 | Rose |
| 10,064,631 B2 | 9/2018 | Dacosta et al. |
| 10,159,499 B2 | 12/2018 | Dacosta et al. |
| 10,292,713 B2 | 5/2019 | Fallin et al. |
| 10,327,829 B2 | 6/2019 | Dacosta et al. |
| 2002/0099381 A1 | 7/2002 | Maroney |
| 2002/0107519 A1 | 8/2002 | Dixon et al. |
| 2002/0165552 A1 | 11/2002 | Duffner |
| 2002/0198531 A1 | 12/2002 | Millard et al. |
| 2004/0010259 A1 | 1/2004 | Keller et al. |
| 2004/0039394 A1 | 2/2004 | Conti et al. |
| 2004/0097946 A1 | 5/2004 | Dietzel et al. |
| 2004/0138669 A1 | 7/2004 | Horn |
| 2005/0004676 A1 | 1/2005 | Schon et al. |
| 2005/0059978 A1 | 3/2005 | Sherry et al. |
| 2005/0070909 A1 | 3/2005 | Egger et al. |
| 2005/0075641 A1 | 4/2005 | Singhatat et al. |
| 2005/0101961 A1 | 5/2005 | Huebner et al. |
| 2005/0149042 A1 | 7/2005 | Metzger |
| 2005/0228389 A1 | 10/2005 | Stiernborg |
| 2005/0251147 A1 | 11/2005 | Novak |
| 2005/0273112 A1 | 12/2005 | McNamara |
| 2006/0129163 A1 | 6/2006 | McGuire |
| 2006/0206044 A1 | 9/2006 | Simon |
| 2006/0217733 A1 | 9/2006 | Plassky et al. |
| 2006/0229621 A1 | 10/2006 | Cadmus |
| 2006/0241607 A1 | 10/2006 | Myerson et al. |
| 2006/0241608 A1 | 10/2006 | Myerson et al. |
| 2006/0264961 A1 | 11/2006 | Murray-Brown |
| 2007/0010818 A1 | 1/2007 | Stone et al. |
| 2007/0123857 A1 | 5/2007 | Deffenbaugh et al. |
| 2007/0233138 A1 | 10/2007 | Figueroa et al. |
| 2007/0265634 A1 | 11/2007 | Weinstein |
| 2007/0276383 A1 | 11/2007 | Rayhack |
| 2008/0009863 A1 | 1/2008 | Bond et al. |
| 2008/0039850 A1 | 2/2008 | Rowley et al. |
| 2008/0091197 A1 | 4/2008 | Coughlin |
| 2008/0140081 A1 | 6/2008 | Heavener et al. |
| 2008/0147073 A1 | 6/2008 | Ammann et al. |
| 2008/0172054 A1 | 7/2008 | Claypool et al. |
| 2008/0195215 A1 | 8/2008 | Morton |
| 2008/0208252 A1 | 8/2008 | Holmes |
| 2008/0262500 A1 | 10/2008 | Collazo |
| 2008/0269908 A1 | 10/2008 | Warburton |
| 2009/0036893 A1 | 2/2009 | Kartalian et al. |
| 2009/0036931 A1 | 2/2009 | Pech et al. |
| 2009/0054899 A1 | 2/2009 | Ammann et al. |
| 2009/0093849 A1 | 4/2009 | Grabowski |
| 2009/0105767 A1 | 4/2009 | Reiley |
| 2009/0118733 A1 | 5/2009 | Orsak et al. |
| 2009/0198244 A1 | 8/2009 | Leibel |
| 2009/0198279 A1 | 8/2009 | Zhang et al. |
| 2009/0222047 A1 | 9/2009 | Graham |
| 2009/0254092 A1 | 10/2009 | Albiol |
| 2009/0254126 A1 | 10/2009 | Orbay et al. |
| 2009/0287309 A1 | 11/2009 | Walch et al. |
| 2010/0069910 A1 | 3/2010 | Hasselman |
| 2010/0121334 A1 | 5/2010 | Couture et al. |
| 2010/0130981 A1 | 5/2010 | Richards |
| 2010/0152782 A1 | 6/2010 | Stone et al. |
| 2010/0168799 A1 | 7/2010 | Schumer |
| 2010/0185245 A1 | 7/2010 | Paul et al. |
| 2010/0249779 A1 | 9/2010 | Hotchkiss et al. |
| 2010/0256687 A1 | 10/2010 | Neufeld et al. |
| 2010/0318088 A1 | 12/2010 | Warne et al. |
| 2010/0324556 A1 | 12/2010 | Tyber et al. |
| 2011/0093084 A1 | 4/2011 | Morton |
| 2011/0245835 A1 | 10/2011 | Dodds et al. |
| 2011/0288550 A1 | 11/2011 | Orbay et al. |
| 2011/0301648 A1 | 12/2011 | Lofthouse et al. |
| 2012/0016426 A1 | 1/2012 | Robinson |
| 2012/0065689 A1 | 3/2012 | Prasad et al. |
| 2012/0078258 A1 | 3/2012 | Lo et al. |
| 2012/0123420 A1 | 5/2012 | Honiball |
| 2012/0123484 A1 | 5/2012 | Lietz et al. |
| 2012/0130376 A1 | 5/2012 | Loring et al. |
| 2012/0130383 A1 | 5/2012 | Budoff |
| 2012/0184961 A1 | 7/2012 | Johannaber |
| 2012/0185056 A1 | 7/2012 | Warburton |
| 2012/0191199 A1 | 7/2012 | Raemisch |
| 2012/0239045 A1 | 9/2012 | Li |
| 2012/0253350 A1 | 10/2012 | Anthony et al. |
| 2012/0265301 A1 | 10/2012 | Demers et al. |
| 2012/0277745 A1 | 11/2012 | Lizee |
| 2012/0330135 A1 | 12/2012 | Millahn et al. |
| 2013/0012949 A1 | 1/2013 | Fallin et al. |
| 2013/0035694 A1 | 2/2013 | Grimm et al. |
| 2013/0085499 A1 | 4/2013 | Lian |
| 2013/0096563 A1 | 4/2013 | Meade et al. |
| 2013/0131821 A1 | 5/2013 | Cachia |
| 2013/0150903 A1 | 6/2013 | Vincent |
| 2013/0158556 A1 | 6/2013 | Jones et al. |
| 2013/0165936 A1 | 6/2013 | Myers |
| 2013/0165938 A1 | 6/2013 | Chow et al. |
| 2013/0172942 A1 | 7/2013 | Lewis et al. |
| 2013/0184714 A1 | 7/2013 | Kaneyama et al. |
| 2013/0190765 A1 | 7/2013 | Harris et al. |
| 2013/0190766 A1 | 7/2013 | Harris et al. |
| 2013/0204259 A1 | 8/2013 | Zajac |
| 2013/0226248 A1 | 8/2013 | Hatch et al. |
| 2013/0226252 A1 | 8/2013 | Mayer |
| 2013/0231668 A1 | 9/2013 | Olsen et al. |
| 2013/0237987 A1 | 9/2013 | Graham |
| 2013/0237989 A1 | 9/2013 | Bonutti |
| 2013/0267956 A1 | 10/2013 | Terrill et al. |
| 2013/0310836 A1 | 11/2013 | Raub et al. |
| 2013/0325019 A1 | 12/2013 | Thomas et al. |
| 2013/0325076 A1 | 12/2013 | Palmer et al. |
| 2013/0331845 A1 | 12/2013 | Horan et al. |
| 2013/0338785 A1 | 12/2013 | Wong |
| 2014/0005672 A1 | 1/2014 | Edwards et al. |
| 2014/0025127 A1 | 1/2014 | Richter |
| 2014/0039501 A1 | 2/2014 | Schickendantz et al. |
| 2014/0039561 A1 | 2/2014 | Weiner et al. |
| 2014/0046387 A1 | 2/2014 | Waizenegger |
| 2014/0074099 A1 | 3/2014 | Vigneron et al. |
| 2014/0074101 A1 | 3/2014 | Collazo |
| 2014/0094861 A1 | 4/2014 | Fallin |
| 2014/0094924 A1 | 4/2014 | Hacking et al. |
| 2014/0135775 A1 | 5/2014 | Maxson et al. |
| 2014/0163563 A1 | 6/2014 | Reynolds et al. |
| 2014/0171953 A1 | 6/2014 | Gonzalvez et al. |
| 2014/0180342 A1 | 6/2014 | Lowery et al. |

(56) References Cited

U.S. PATENT DOCUMENTS

| | | |
|---|---|---|
| 2014/0188139 A1 | 7/2014 | Fallin et al. |
| 2014/0194884 A1 | 7/2014 | Martin et al. |
| 2014/0194999 A1 | 7/2014 | Orbay et al. |
| 2014/0207144 A1 | 7/2014 | Lee et al. |
| 2014/0249537 A1 | 9/2014 | Wong et al. |
| 2014/0257308 A1 | 9/2014 | Johannaber |
| 2014/0257509 A1 | 9/2014 | Dacosta et al. |
| 2014/0276815 A1 | 9/2014 | Riccione |
| 2014/0276853 A1 | 9/2014 | Long et al. |
| 2014/0277176 A1 | 9/2014 | Buchanan et al. |
| 2014/0277214 A1 | 9/2014 | Helenbolt et al. |
| 2014/0288562 A1 | 9/2014 | Von Zabern et al. |
| 2014/0296995 A1 | 10/2014 | Reiley et al. |
| 2014/0303621 A1 | 10/2014 | Gerold et al. |
| 2014/0336658 A1 | 11/2014 | Luna et al. |
| 2014/0343555 A1 | 11/2014 | Russi et al. |
| 2015/0032168 A1 | 1/2015 | Orsak et al. |
| 2015/0045801 A1 | 2/2015 | Axelson, Jr. et al. |
| 2015/0045839 A1 | 2/2015 | Dacosta et al. |
| 2015/0051650 A1 | 2/2015 | Verstreken et al. |
| 2015/0057667 A1 | 2/2015 | Ammann et al. |
| 2015/0066094 A1 | 3/2015 | Prandi et al. |
| 2015/0112446 A1 | 4/2015 | Melamed et al. |
| 2015/0119944 A1 | 4/2015 | Geldwert |
| 2015/0142064 A1 | 5/2015 | Perez et al. |
| 2015/0150608 A1 | 6/2015 | Sammarco |
| 2015/0182273 A1 | 7/2015 | Stemniski et al. |
| 2015/0223851 A1 | 8/2015 | Hill et al. |
| 2015/0245858 A1 | 9/2015 | Weiner et al. |
| 2016/0015426 A1 | 1/2016 | Dayton |
| 2016/0022315 A1 | 1/2016 | Soffiatti et al. |
| 2016/0151165 A1 | 6/2016 | Fallin et al. |
| 2016/0175089 A1 | 6/2016 | Fallin et al. |
| 2016/0192950 A1 | 7/2016 | Dayton et al. |
| 2016/0199076 A1 | 7/2016 | Fallin et al. |
| 2016/0213384 A1 | 7/2016 | Fallin et al. |
| 2016/0235414 A1 | 8/2016 | Hatch et al. |
| 2016/0242791 A1 | 8/2016 | Fallin et al. |
| 2016/0256204 A1 | 9/2016 | Patel et al. |
| 2016/0324532 A1 | 11/2016 | Montoya et al. |
| 2016/0354127 A1 | 12/2016 | Lundquist et al. |
| 2017/0042598 A1 | 2/2017 | Santrock et al. |
| 2017/0143511 A1 | 5/2017 | Cachia |
| 2017/0164989 A1 | 6/2017 | Weiner et al. |
| 2018/0344334 A1 | 12/2018 | Kim et al. |

FOREIGN PATENT DOCUMENTS

| | | |
|---|---|---|
| CA | 2854997 A1 | 5/2013 |
| CH | 695846 A5 | 9/2006 |
| CN | 2930668 Y | 8/2007 |
| CN | 201558162 U | 8/2010 |
| CN | 201572172 U | 9/2010 |
| CN | 201586060 U | 9/2010 |
| CN | 201912210 U | 8/2011 |
| CN | 101237835 B | 11/2012 |
| CN | 202801773 U | 3/2013 |
| CN | 103462675 A | 12/2013 |
| CN | 103505276 A | 1/2014 |
| CN | 203458450 U | 3/2014 |
| CN | 102860860 B | 5/2014 |
| CN | 203576647 U | 5/2014 |
| CN | 104490460 A | 4/2015 |
| CN | 104510523 A | 4/2015 |
| CN | 104523327 A | 4/2015 |
| CN | 104546102 A | 4/2015 |
| CN | 204379413 U | 6/2015 |
| CN | 204410951 U | 6/2015 |
| CN | 204428143 U | 7/2015 |
| CN | 204428144 U | 7/2015 |
| CN | 204428145 U | 7/2015 |
| CN | 204446081 U | 7/2015 |
| DE | 202006010241 U1 | 3/2007 |
| DE | 102007053058 B3 | 4/2009 |
| EP | 685206 B1 | 9/2000 |
| EP | 1508316 B1 | 5/2007 |
| EP | 1897509 B1 | 7/2009 |
| EP | 2124772 A1 | 12/2009 |
| EP | 2124832 B1 | 8/2012 |
| EP | 2632349 A1 | 9/2013 |
| EP | 2665428 A1 | 11/2013 |
| EP | 2742878 A1 | 6/2014 |
| EP | 2750617 A1 | 7/2014 |
| EP | 2849684 A1 | 3/2015 |
| EP | 2624764 B1 | 12/2015 |
| FR | 2362616 A1 | 3/1978 |
| FR | 2764183 B1 | 11/1999 |
| FR | 2953120 B1 | 1/2012 |
| FR | 3030221 A1 | 6/2016 |
| GB | 2154143 A | 9/1985 |
| GB | 2154144 A | 9/1985 |
| GB | 2334214 B | 1/2003 |
| IN | 200903719 P1 | 6/2009 |
| IN | 200904479 P2 | 5/2010 |
| IN | 140/DELNP/2012 P1 | 2/2013 |
| IN | 2004/KOLNP/2013 P2 | 11/2013 |
| JP | 4134243 B2 | 8/2008 |
| JP | 4162380 B2 | 10/2008 |
| JP | 2011092405 A | 5/2011 |
| JP | 2011523889 A | 8/2011 |
| JP | 4796943 B2 | 10/2011 |
| JP | 5466647 B2 | 4/2014 |
| JP | 2014511207 A | 5/2014 |
| JP | 2014521384 A | 8/2014 |
| JP | 5628875 B2 | 11/2014 |
| KR | 100904142 B1 | 6/2009 |
| RU | 2098036 C1 | 12/1997 |
| RU | 2195892 C2 | 1/2003 |
| RU | 2320287 C1 | 3/2008 |
| RU | 2321366 C2 | 4/2008 |
| RU | 2321369 C1 | 4/2008 |
| RU | 2346663 C2 | 2/2009 |
| RU | 2412662 C1 | 2/2011 |
| SU | 1333328 A2 | 8/1987 |
| WO | 0166022 A1 | 9/2001 |
| WO | 03075775 A1 | 9/2003 |
| WO | 2004089227 A2 | 10/2004 |
| WO | 2008051064 A1 | 5/2008 |
| WO | 2009029798 A1 | 3/2009 |
| WO | 2009032101 A2 | 3/2009 |
| WO | 2011037885 A1 | 3/2011 |
| WO | 2012029008 A1 | 3/2012 |
| WO | 2013090392 A1 | 6/2013 |
| WO | 2013134387 A1 | 9/2013 |
| WO | 2013169475 A1 | 11/2013 |
| WO | 2014020561 A1 | 2/2014 |
| WO | 2014022055 A1 | 2/2014 |
| WO | 2014035991 A1 | 3/2014 |
| WO | 2014085882 A1 | 6/2014 |
| WO | 2014147099 A1 | 9/2014 |
| WO | 2014152219 A2 | 9/2014 |
| WO | 2014152535 A1 | 9/2014 |
| WO | 2014177783 A1 | 11/2014 |
| WO | 2014200017 A1 | 12/2014 |
| WO | 2015094409 A1 | 6/2015 |
| WO | 2015105880 A1 | 7/2015 |
| WO | 2015127515 A2 | 9/2015 |
| WO | 2016134160 A1 | 8/2016 |

OTHER PUBLICATIONS

Saltzman et al., "Prospective Controlled Trial of STAR Total Ankle Replacement Versus Ankle Fusion: Initial Results," Foot & Ankle International, vol. 30, No. 7, Jul. 2009, pp. 579-596.

Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).

Scranton Jr. et al, "Anatomic Variations in the First Ray: Part I. Anatomic Aspects Related to Bunion Surgery," Clinical Orthopaedics and Related Research, vol. 151, Sep. 1980, pp. 244-255.

(56) References Cited

OTHER PUBLICATIONS

Siddiqui et al. "Fixation of Metatarsal Fracture With Bone Plate in a Dromedary Heifer," Open Veterinary Journal, vol. 3, No. 1, 2013, pp. 17-20.
Sidekick Stealth Rearfoot Fixator, Wright Medical Technology, Surgical Technique, Dec. 2, 2013, 20 pages.
Simpson et al., "Computer-Assisted Distraction Ostegogenesis by Ilizarov's Method," International Journal of Medical Robots and Computer Assisted Surgery, vol. 4, No. 4, Dec. 2008, pp. 310-320, (Abstract Only).
Small Bone External Fixation System, Acumed, Surgical Technique, Effective date Sep. 2014, 8 pages.
"Smith & Nephew scores a HAT-TRICK with its entry into the high-growth hammer toe repair market," Smith & Nephew, Jul. 31, 2014, 2 pages.
Stableloc External Fixation System, Acumed, Product Overview, Effective date Sep. 2015, 4 pages.
Stahl et al., "Derotation of Post-Traumatic Femoral Deformities by Closed Intramedullary Sawing," Injury, vol. 37, No. 2, Feb. 2006, pp. 145-151, (Abstract Only).
Talbot et al.,"Assessing Sesamoid Subluxation: How Good is the AP Radiograph?," Foot and Ankle International, vol. 19, No. 8, Aug. 1998, pp. 547-554.
TempFix Spanning the Ankle Joint Half Pin and Transfixing Pin Techniques, Biomet Orthopedics, Surgical Technique, 2012, 16 pages.
Tricot et al., "3D-corrective osteotomy using surgical guides for posttraumatic distal humeral deformity," Acta Orthopaedica Belgica, vol. 78, No. 4, 2012, pp. 538-542.
Vitek et al., "Die Behandlung des Hallux rigidus mit Cheilektomie und Akin-Moberg-Osteotomie unter Verwendung einer neuen Schnittlehre und eines neuen Schraubensystems," Orthopadische Praxis, vol. 44, Nov. 2008, pp. 563-566, including English Abstract on p. 564.
Vitek, "Neue Techniken in der Fußchirurgie Das V-tek-System," ABW Wissenschaftsverlag GmbH, 2009, 11 pages, including English Abstract.
Weber et al., "A Simple System for Navigation of Bone Alignment Osteotomies of the Tibia," International Congress Series, vol. 1268, Jan. 2004, pp. 608-613, (Abstract Only).
Weil et al., "Anatomic Plantar Plate Repair Using the Weil Metatarsal Osteotomy Approach," Foot & Ankle Specialist, vol. 4, No. 3, 2011, pp. 145-150.
Wendl et al., "Navigation in der Knieendoprothetik," OP-Journal, vol. 17, 2002, pp. 22-27, including English Abstract.
Whipple et al., "Zimmer Herbert Whipple Bone Screw System: Surgical Techniques for Fixation of Scaphoid and Other Small Bone Fractures," Zimmer, 2003, 59 pages.
Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).
Yasuda et al., "Proximal Supination Osteotomy of the First Metatarsal for Hallux Valgus," Foot and Ankle International, vol. 36, No. 6, Jun. 2015, pp. 696-704.
"Accu-Cut Osteotomy Guide System," BioPro, Brochure, Oct. 2018, 2 pages.
"Acumed Osteotomiesystem Operationstechnik," Acumed, 2014, 19 pages (including 3 pages English translation).
Albano et al., "Biomechanical Study of Transcortical or Transtrabecular Bone Fixation of Patellar Tendon Graft wih Bioabsorbable Pins in ACL Reconstruction in Sheep," Revista Brasileira de Ortopedia (Rev Bras Ortop.) vol. 47, No. 1, 2012, pp. 43-49.
Anderson et al., "Uncemented STAR Total Ankle Prostheses," The Journal of Bone and Joint Surgery, vol. 86(1, Suppl 2), Sep. 2004, pp. 103-111, (Abstract Only).
Blomer, "Knieendoprothetik—Herstellerische Probleme und technologische Entwicklungen," Orthopade, vol. 29, 2000, pp. 688-696, including English Abstract on p. 689.

Bouaicha et al., "Fixation of Maximal Shift Scarf Osteotomy with Inside-Out Plating: Technique Tip," Foot & Ankle International, vol. 32, No. 5, May 2011, pp. 567-569.
Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.
Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, vol. 53, 2014, pp. 584-587.
Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot and Ankle Surgery, vol. 52, No. 3, May/Jun. 2013, pp. 348-354.
Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.
De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.
DiDomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.
Dobbe et al. "Patient-Tailored Plate for Bone Fixation and Accurate 3D Positioning in Corrective Osteotomy," Medical and Biological Engineering and Computing, vol. 51, No. 1-2, Feb. 2013, pp. 19-27, (Abstract Only).
EBI Extra Small Rail Fixator, Biomet Trauma, retrieved Dec. 19, 2014, from the Internet: <http://footandanklefixation.com/product/biomet-trauma-ebi-extra-small-rail-fixator>, 7 pages.
"Futura Forefoot Implant Arthroplasty Products," Tornier, Inc., 2008, 14 pages.
Garthwait, "Accu-Cut System Facilitates Enhanced Precision," Podiatry Today, vol. 18, No. 6, Jun. 2005, 6 pages.
Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.
Gotte, "Entwicklung eines Assistenzrobotersystems für die Knieendoprothetik," Forschungsberichte, Technische Universitat Munchen, 165, 2002, 11 pages, including partial English Translation.
Gregg et al., "Plantar plate repair and Weil osteotomy for metatarsophalangeal joint instability," Foot and Ankle Surgery, vol. 13, 2007, pp. 116-121.
Grondal et al., "A Guide Plate for Accurate Positioning of First Metatarsophalangeal Joint during Fusion," Operative Orthopädie Und Traumatologie, vol. 16, No. 2, 2004, pp. 167-178 (Abstract Only).
"HAT-TRICK Lesser Toe Repair System," Smith & Nephew, Brochure, Aug. 2014, 12 pages.
"HAT-TRICK Lesser Toe Repair System, Foot and Ankle Technique Guide, Metatarsal Shortening Osteotomy Surgical Technique," Smith & Nephew, 2014, 16 pages.
Hetherington et al., "Evaluation of surgical experience and the use of an osteotomy guide on the apical angle of an Austin osteotomy," The Foot, vol. 18, 2008, pp. 159-164.
Hirao et al., "Computer assisted planning and custom-made surgical guide for malunited pronation deformity after first metatarsophalangeal joint arthrodesis in rheumatoid arthritis: A case report," Computer Aided Surgery, vol. 19, Nos. 1-3, 2014, pp. 13-19.
"Hoffmann II Compact External Fixation System," Stryker, Brochure, Literature No. 5075-1-500, 2006, 12 pages.
"Hoffmann II Micro Lengthener," Stryker, Operative Technique, Literature No. 5075-2-002, 2008, 12 pages.

(56) References Cited

OTHER PUBLICATIONS

"Hoffmann Small System External Fixator Orthopedic Instruments," Stryker, retrieved Dec. 19, 2014, from the Internet: <http://www.alibaba.com/product-detail/Stryker-Hoffmann-Small-System-External-Fixator_1438850129.html>, 3 pages.

Kim et al., "A New Measure of Tibial Sesamoid Position in Hallux Valgus in Relation to the Coronal Rotation of the First Metatarsal in CT Scans," Foot and Ankle International, vol. 36, No. 8, 2015, pp. 944-952.

"Lag Screw Target Bow," Stryker Leibinger GmbH & Co. KG, Germany 2004, 8 pages.

Lieske et al., "Implantation einer Sprunggelenktotalendo-prothese vom Typ Salto 2," Operative Orthopädie und Traumatologie, vol. 26, No. 4, 2014, pp. 401-413, including English Abstract on p. 403.

MAC (Multi Axial Correction) Fixation System, Biomet Trauma, retrieved Dec. 19, 2014, from the Internet: <http://footandanklefixation.com/product/biomet-trauma-mac-multi-axial-correction-fixation-system>, 7 pages.

Magin, "Computemavigierter Gelenkersatz am Knie mit dem Orthopilot," Operative Orthopädie und Traumatologie, vol. 22, No. 1, 2010, pp. 63-80, including English Abstract on p. 64.

Magin, "Die belastungsstabile Lapidus-Arthrodese bei Hallux-valgus-Deformität mittels IVP-Plattenfixateur (V-TEK-System)," Operative Orthopädie und Traumatologie, vol. 26, No. 2, 2014, pp. 184-195, including English Abstract on p. 186.

Michelangelo Bunion System, Surgical Technique, Instratek Incorporated, publication date unknown, 4 pages.

Mini Joint Distractor, Arthrex, retrieved Dec. 19, 2014, from the Internet: <http://www.arthrex.com/foot-ankle/mini-joint-distractor/products>, 2 pages.

MiniRail System, Small Bone Innovations, Surgical Technique, 2010, 24 pages.

Miyake et al., "Three-Dimensional Corrective Osteotomy for Malunited Diaphyseal Forearm Fractures Using Custom-Made Surgical Guides Based on Computer Simulation," JBJS Essential Surgical Techniques, vol. 2, No. 4, 2012, 11 pages.

Modular Rail System: External Fixator, Smith & Nephew, Surgical Technique, 2013, 44 pages.

Monnich et al., "A Hand Guided Robotic Planning System for Laser Osteotomy in Surgery," World Congress on Medical Physics and Biomedical Engineering vol. 25/6: Surgery, Nimimal Invasive Interventions, Endoscopy and Image Guided Therapy, Sep. 7-12, 2009, pp. 59-62, (Abstract Only).

Moore et al., "Effect of Ankle Flexion Angle on Axial Alignment of Total Ankle Replacement," Foot and Ankle International, vol. 31, No. 12, Dec. 2010, pp. 1093-1098, (Abstract Only).

Mortier et al., "Axial Rotation of the First Metatarsal Head in a Normal Population and Hallux Valgus Patients," Orthopaedics and Traumatology: Surgery and Research, vol. 98, 2012, pp. 677-683.

Nagy et al., "The AO Ulnar Shortening Osteotomy System Indications and Surgical Technique," Journal of Wrist Surgery, vol. 3, No. 2, 2014, pp. 91-97.

NexFix from Nexa Orthopedics, MetaFix I from Merete Medical, Inc. and The BioPro Lower Extremities from BioPro, found in Foot & Ankle International Journal, vol. 28, No. 1, Jan. 2007, 4 pages.

Odenbring et al., "A guide instrument for high tibial osteotomy," Acta Orthopaedica Scandinavica, vol. 60, No. 4, 1989, pp. 449-451.

Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.

Otsuki et al., "Developing a novel custom cutting guide for curved per-acetabular osteotomy," International Orthopaedics (SICOT), vol. 37, 2013, pp. 1033-1038.

"Patient to Patient Precision, Accu-Cut, Osteotomy Guide System," BioPro, Foot & Ankle International Journal, vol. 23, No. 8, Aug. 2002, 2 pages.

Peters et al., "Flexor Hallucis Longus Tendon Laceration as a Complication of Total Ankle Arthroplasty," Foot & Ankle International, vol. 34, No. 1, 2013, pp. 148-149.

"Prophecy Inbone Preoperative Navigation Guides," Wright Medical Technology, Inc., Nov. 2013, 6 pages.

"RAYHACK Ulnar Shortening Generation II Low-Profile Locking System Surgical Technique," Wright Medical Technology, Inc., Dec. 2013, 20 pages.

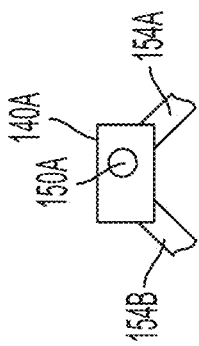
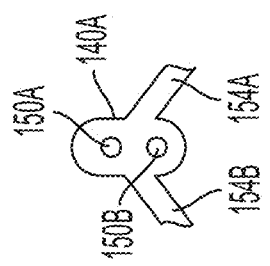
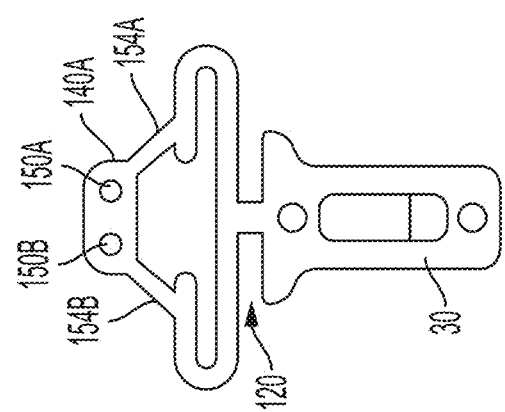

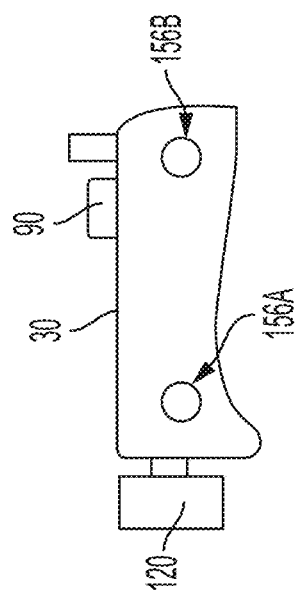

BONE CUTTING GUIDE SYSTEMS AND METHODS

RELATED APPLICATION

This application is a continuation of U.S. patent application Ser. No. 15/603,056, filed May 23, 2017, which is a continuation of U.S. patent application Ser. No. 14/990,574, filed Jan. 7, 2016, and issued as U.S. Pat. No. 9,687,250 on Jun. 27, 2017, which in turn claims the benefit of U.S. Provisional Application Ser. No. 62/100,641, filed Jan. 7, 2015. The entire contents of each of these applications are hereby incorporated by reference.

TECHNICAL FIELD

This disclosure relates generally to devices and methods for positioning and cutting bones.

BACKGROUND

Bones, such as the bones of a foot, may be anatomically misaligned. In certain circumstances, surgical intervention is required to correctly align the bones to reduce patient discomfort and improve patient quality of life.

SUMMARY

In general, this disclosure is directed to bone cutting guide systems and techniques for cutting bones. In some examples, a bone cutting guide includes a main body, or support, that houses a shaft that can translate relative to the main body. The shaft may have a main guide member positioned on the end of the shaft. The main guide member may define opposed guide surfaces configured to receive a cutting member. For example, the cutting member may be inserted between the opposed guide surfaces and bounded within a range of movement by the guide surfaces, causing the cutting member to be directed at a cutting location under the guide surfaces. Additionally or alternatively, the main guide member may define a single cutting surface/plane. The cutting surface/plane may be a surface against which a clinician can position a cutting member and then guide the cutting member along the cutting surface/plane to perform a cutting operation.

The main body of the bone cutting guide can include fixation members, such as fixation pins or apertures, that allow the main body to be fixated on or adjacent a bone to be cut. For example, in use, a clinician may fixate the main body to a bone (e.g., a first metatarsal). Thereafter, the clinician may translate the main guide member having at least one cutting guide surface (e.g., opposed cutting guide surfaces) relative to the fixed main body. The clinician can translate the main guide member by sliding or rotating the shaft housed within the main body, e.g., causing the distal end of the shaft and main guide member carried thereon away from or towards the main body. Once suitably positioned, the clinician may or may not lock the location of the shaft and perform one or more cuts through the guide surfaces of the main guide member.

In some configurations, the bone cutting guide also includes a bridge component that can form a bridge over a section of bone, such as a joint between adjacent bones (e.g., first metatarsal-medial cuneiform joint). For example, the bridge component may have a proximal end that is attachable to the main guide member carried on the shaft attached to the main body and a distal end separated by one or more rails. The proximal end may be insertable between the opposed cutting guide surfaces of the main guide member, e.g., such that the proximal end of the bridge can be inserted between the guide surfaces after performing a cut through the guide surfaces. The distal end of the bridging member can include fixation members, such as fixation pins or apertures, that allow the distal end of the bridging member to be fixated to bone. In one application, the distal end of the bridging member is fixated to a different bone than the bone the main body is fixated to such that the bridging member spans a joint. In such applications, joint spacing may be expanded or contracted by translating the shaft carried by the main body.

In addition to or in lieu of providing a bridging member, in some additional configurations, the bone cutting guide may include a secondary guide member. The secondary guide member can be positioned distally of the main guide member and may also include guide surfaces, such as opposed guide surfaces forming a channel sized and shaped to receive a cutting member. The secondary guide member may facilitate making a second bone cut distal of a location where a first bone cut is made using the main guide member.

In one example, a bone cutting guide is described that includes a support defining an inner cavity and a shaft disposed at least partially within the inner cavity, where the shaft is translatable within the inner cavity relative to the support. The bone cutting guide also includes a main guide member located on an end of the shaft, where the main guide member includes a first guide surface defining a first plane and a second guide surface defining a second plane, and where the first plane is parallel to the second plane.

In another example, a method for cutting bones is described. The method includes fixing a support to a bone and aligning a main guide member to be positioned at a location to be cut. The method further includes making a first cut at the location to be cut by inserting a cutting member through a space defined between a first guide surface of the main guide member and a second guide surface of the main guide member.

The details of one or more examples are set forth in the accompanying drawings and the description below. Other features, objects, and advantages will be apparent from the description and drawings, and from the claims.

BRIEF DESCRIPTION OF THE DRAWINGS

FIGS. 3B-3D are top plan view illustrations of a bone cutting guide with different example connecting blocks.

FIG. 3E is a side plan view of a bone cutting guide and an exemplary support.

DETAILED DESCRIPTION

The following detailed description is exemplary in nature and is not intended to limit the scope, applicability, or configuration of the invention in any way. Rather, the following description provides some practical illustrations for implementing exemplary embodiments of the present invention. Examples of constructions, materials, and dimensions are provided for selected elements, and all other elements employ that which is known to those of ordinary skill in the field of the invention. Those skilled in the art will recognize that many of the noted examples have a variety of suitable alternatives.

Embodiments of the present invention include a bone cutting guide. In an exemplary application, the bone cutting guide can be useful during a surgical procedure, such as a bone alignment, osteotomy, fusion procedure, and/or other procedures where one or more bones are to be cut. Such a procedure can be performed, for example, on bones (e.g., adjacent bones separated by a joint or different portions of a single bone) in the foot or hand, where bones are relatively smaller compared to bones in other parts of the human anatomy. In one example, a procedure utilizing the bone cutting guide can be performed to correct an alignment between a metatarsal (e.g. a first metatarsal) and a cuneiform (e.g., a first cuneiform), such as a bunion correction. An example of such a procedure is a lapidus procedure. In another example, the procedure can be performed by modifying an alignment of a metatarsal (e.g. a first metatarsal). An example of such a procedure is a basilar metatarsal osteotomy procedure.

Figure 1:
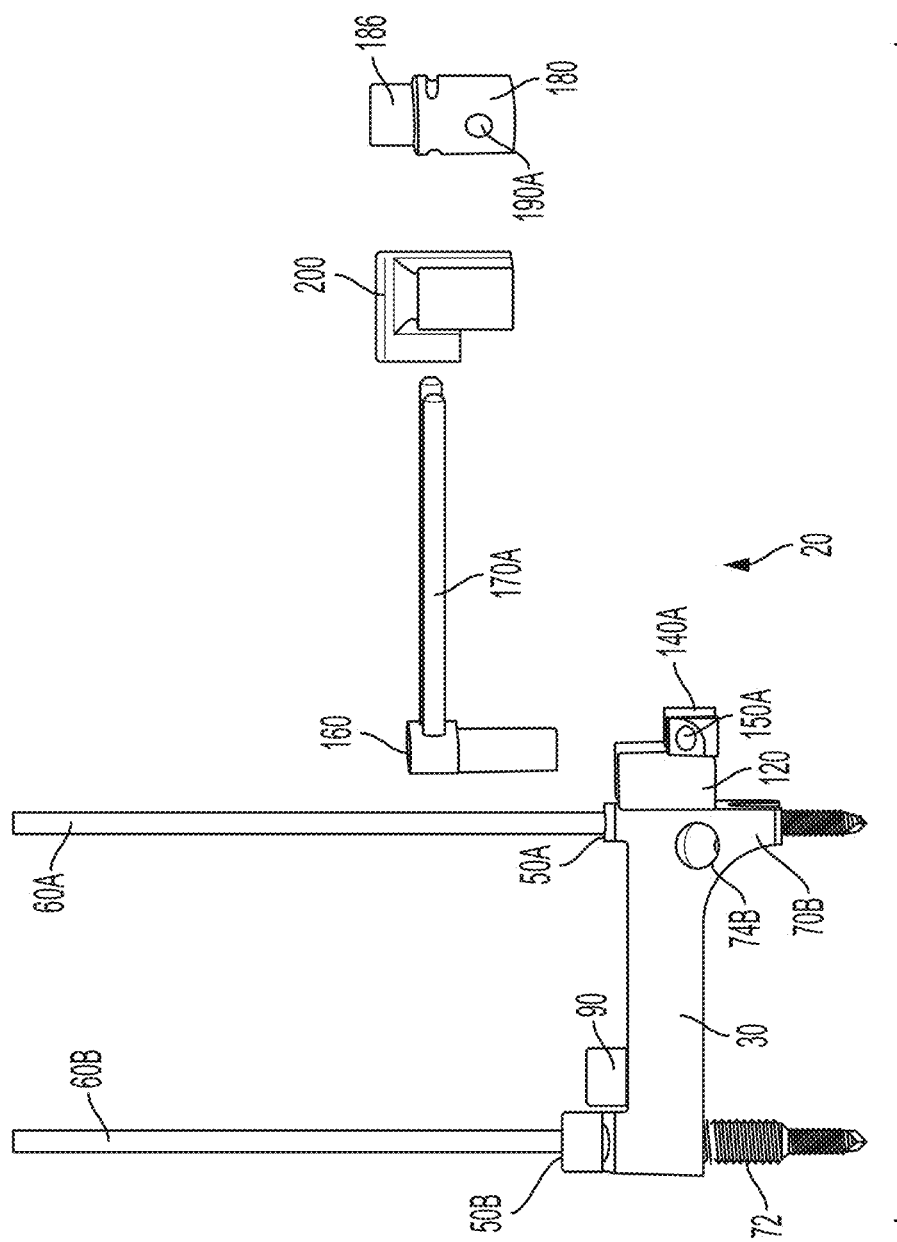
FIG. 1 is a side view of an embodiment of a bone cutting guide, with some components shown in an exploded view.
Figure 2:
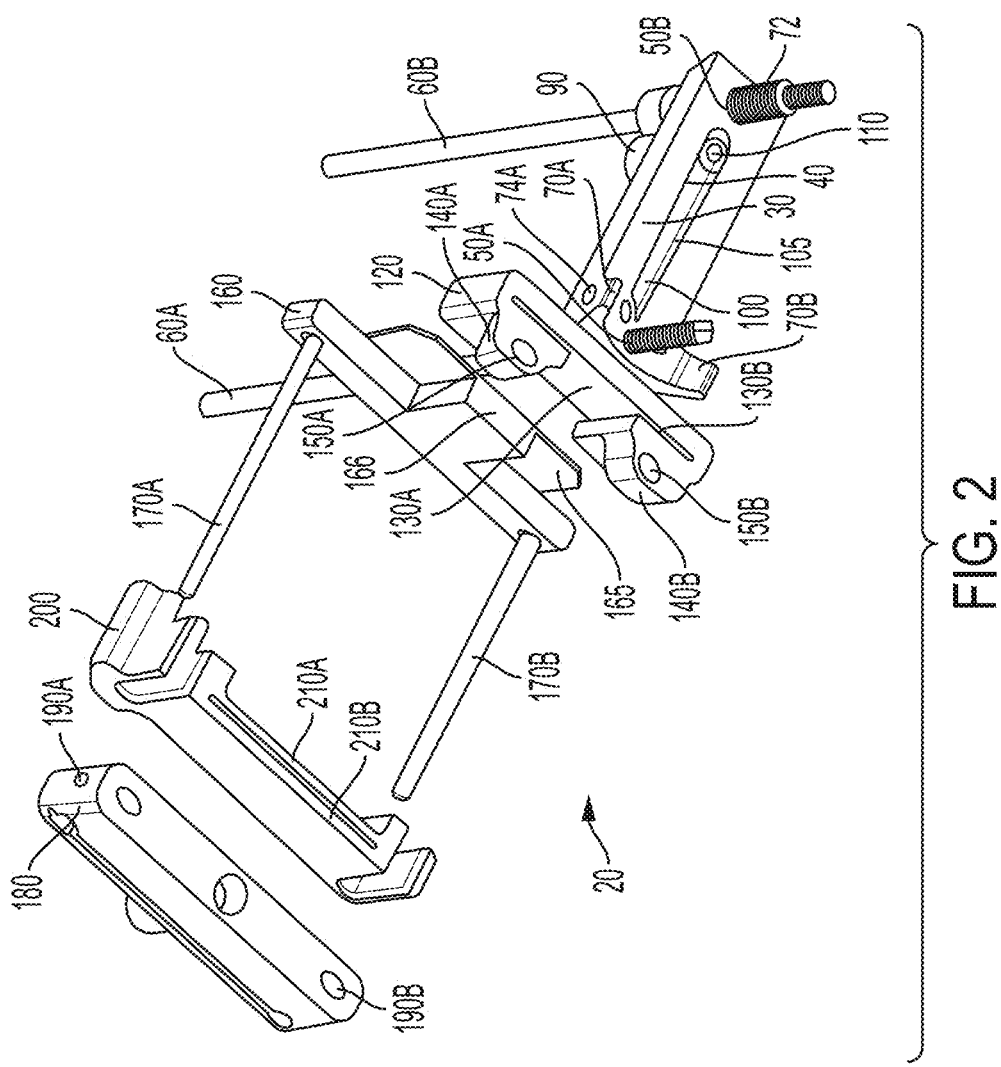
FIG. 2 is a perspective view of the bone cutting guide of FIG. 1.
Figure 3A:
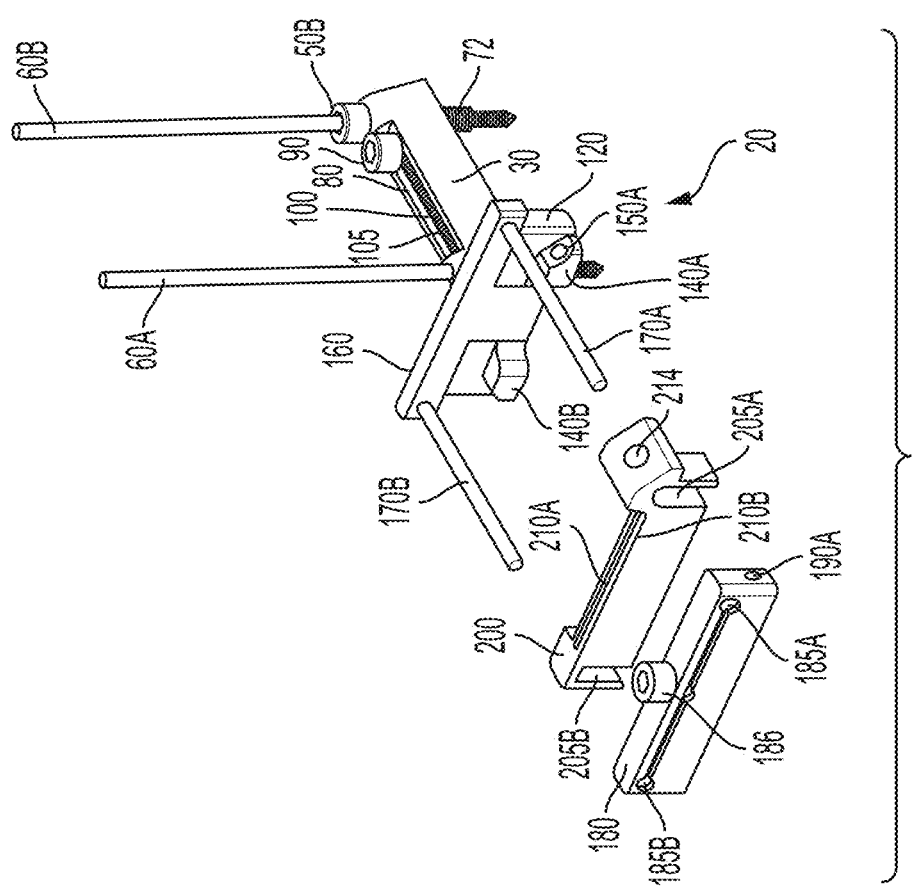
FIG. 3A is a perspective view of the bone cutting guide of FIG. 1 with a bridge component attached to a main guide member.

FIGS. 1, 2, and 3A show an embodiment of a bone cutting guide 20 with some components of the bone cutting guide 20 shown in an exploded view. FIG. 1 is a side view of the bone cutting guide 20, while FIGS. 2 and 3A are perspective views of the bone cutting guide 20. The bone cutting guide 20 can include a support 30 which defines an inner cavity 40 (FIG. 2). In one embodiment, the support 30 can include a first fixation aperture 50A and a second fixation aperture 50B, each of which can extend through the support 30 and receive fixation pins 60A and 60B, respectively, such that the fixation pins 60A and 60B extend through the support 30 via the fixation apertures 50A and 50B. In the embodiment shown, the fixation pins 60A and 60B have a threaded first end adapted to threadingly engage with a bone, and allow the support 30 to be translated along a longitudinal axis of both pins 60A and 60B. In the illustrated embodiments, the fixation apertures 50A and 50B are located on opposite longitudinal ends of the support 30, but in other embodiments the fixation apertures 50A and 50B can be located at various positions on the support 30.

The support 30 can further include one or more extensions 70A and/or 70B protruding generally radially out from the support 30, which may define a concave surface configured to receive a generally cylindrical bone portion. In the embodiment shown, fixation aperture 50B is provided with an extension member 72 which can be threadingly coupled to the support 30. Such an extension member 72 can be adjusted relative to the support 30 to allow the support to become parallel with a longitudinal axis of a bone, if desired. In such embodiments, the support 30 can rest on a bone via the extensions 70 AB and extension member 72 in a position generally parallel to the bone. Fixation pin 60B may be received within an internal aperture of the extension member 72. As shown, apertures 74A and B, such as tapered apertures, may be provided proximal to extensions 70 A and B. Such apertures may extend through the support at a skewed angle relative to the longitudinal axis of the support, and may be used to engage a clamping instrument or receive fixation pins.

The support 30 can also include a slot 80 formed on at least a portion of a surface of the support 30. As illustrated in the embodiment of the cutting guide 20 shown in FIG. 3A, the slot 80 can extend in a surface of the support 30 between fixation apertures 50A and 50B. A securing component 90 can be configured to translate along the slot 80 relative to the support 30. For example, the securing component 90 can have a first end with a diameter greater than a diameter of a second opposite end, such that the first end of the securing component 90 is supported by the slot 80 (e.g., the first end has a diameter greater than a radial width of the slot 80) while the second end of the securing component 90 is positioned within the slot 80 (e.g., the second end has a diameter less than a radial width of the slot 80).

The inner cavity 40 of the support 30 can have a shaft 100 positioned at least partially within the inner cavity 40. The shaft 100 can be configured to translate within the inner cavity 40 relative to the support 30, such that an end of the shaft 100 can be made to project out from the inner cavity 40. The shaft 100 may define a slot 105 which may be aligned with the slot 80 defined by the support 30. This slot 105 may receive the pin 60A to reduce interference when the shaft 100 translates. Furthermore, the shaft 100 can include a securing aperture 110 which can be configured to receive at least a portion of the securing component 90. In one embodiment, both the second end of the securing component 90, within the slot 80, and the securing aperture 110 can be threaded to allow the securing component 90 to mate with the securing aperture 110. Such a configuration can allow the shaft 100 to be fixed, such as by compressing a surface of the support 30 that defines the slot 80, and thus prevented from translating within the inner cavity 40, relative to the support 30. In another embodiment, the securing component 90 can be threadingly engaged with the support 30 to act against the shaft 100 to prevent the shaft 100 from traveling with the cavity 40 when desired.

On an end of the shaft 100, a main guide member 120 can be disposed. In some embodiments the main guide member 120 can be integral with the shaft 100, or in other embodiments the main guide member 120 and the shaft 100 can be separate components coupled together. The main guide member 120 can have a first guide surface 130A and a second guide surface 130B, and in some embodiments the main guide member 120 can include blocks 140A and/or

140B. The first and second guide surfaces 130A and 130B can be adjacent surfaces facing one another with a space defined between the first and second guide surfaces 130A and 130B. For example, the first guide surface 130A can be a surface of the main guide member 120 immediately opposite a surface of the main guide member 120 that interfaces with the shaft 100, and the second guide surface 130B can be a surface of the main guide member 120 immediately opposite a surface of the main guide member 120 that includes blocks 140A and 140B.

In the illustrated embodiment, the second guide surface 130B contains a gap, such that the second guide surface 130B is not a single, continuous surface. In other embodiments, the second guide surface 130B can be a single, continuous surface lacking any such gap. The first guide surface 130A defines a first plane, while the second guide surface 130B defines a second plane. As shown, the first guide surface 130A and the second guide surface 130B can be configured such that the first plane is parallel to the second plane, with the space between. In further embodiments (not illustrated), the guide surfaces 130A and 130B can be configured such that the first and/or second planes are skewed.

As previously noted, a surface of the main guide member 120 can include one or more blocks 140A and 140B, either integral with the main guide member 120 or as separate components attached to the main guide member 120. As shown, the blocks 140A and 140B can be on a surface on a side of the main guide member 120 furthest from the interface with the shaft 100. In other applications, the blocks 140A and 140B can be located at various other positions on the main guide member 120. The blocks 140A and 140B can include fixation apertures 150A and 150B respectively. The fixation apertures 150A and 150B extend through the blocks 140A and 140B and provide a location for configuring additional fixation pins to, for example, position a bone or bones.

As shown in FIGS. 3B-3D, the main guide member 120 and at least one block 140A can assume other configurations. In FIG. 3B, the block 140A includes fixation apertures 150A and B and is spaced from the guide surfaces a distance via connecting flanges 154A and 154B. In the embodiment of FIG. 3B, the fixation apertures 150A and B are positioned in a line substantially parallel to the guide surfaces. In FIG. 3C, the orientation of the fixation apertures 150A and B is substantially perpendicular to the guide surfaces. In FIG. 3D, only one fixation aperture 150A is provided.

Another embodiment of a support 30 is depicted in FIG. 3E. In FIG. 3E, the support 30 has at least one (e.g., two) fixation aperture 156A and 156B formed in its side to receive fixation pins. Such apertures can also be included on the opposite side of the support (not shown). In some embodiments, the fixation apertures 156A and 156B can be positioned in a line substantially parallel with a longitudinal axis of the support, and can extend in a direction substantially perpendicular to the longitudinal axis of the support. In certain embodiments, the apertures extend at an angle, such as about 20 degrees, from vertical. In such embodiments, the support 30 can be placed on a dorsal surface and after a first cut or cuts, can be rotated about a pin extending though one of the fixation apertures 156A and 156B to rotate the support relative to the bone and first cut or cuts. The support can then be further pinned to the bone and an additional cut or cuts can be made at a desired angle relative to the first cut or cuts.

In addition to the support 30, the bone cutting guide 20 can include a bridge component 160. As shown in FIG. 3A, the bridge component 160 can attach to the main guide member 120. In particular, in some applications of the bone cutting guide 20, the bridge component 160 can have a geometry that allows the bridge component 160 to attach to the main guide member 120 between the first and second guide surfaces 130A and 130B through an interference fit. Optionally, a locking mechanism can be provided to lock the bridge component to the main guide member, such as a locking tab, screw, pin, cam, etc. For example, the bridge component 160 may have a planar member 165 (shown in FIG. 2) that is received within the gap between the surfaces 130A and 130B and an extending block 166 (shown in FIG. 2) adapted to extend into the surface gap of 130B. In other applications, the bridge component 160 can be coupled to the main guide member 120 by any attachment mechanism, such as screws or clamps. The bridge component 160 can include rails 170A and 170B, each extending out from the bridge component 160 in a same general direction. In other embodiments, the rails 170A and 170B can extend out from the bridge component 160 at different angles.

The bone cutting guide 20 can also include in some embodiments a fixating structure 180. The fixating structure 180 can be supported on the rails 170A and 170B. For example, the fixating structure 180 can include apertures 185A and 185B to receive the rails 170A and 170B, respectively. The fixating structure 180 can be secured to the rails 170A and 170B, such that the fixating structure 180 is obstructed from translating along the rails 170A and 170B, by turning or otherwise actuating an actuator 186 of the fixating structure 180, which moves a lock (not shown) to act against the rails. Furthermore, the fixating structure 180 can also include one or more fixation apertures 190A and/or 190B. Fixation apertures 190A and 190B extend through fixating structure 180 and can be located on opposite ends of the fixating structure 180, at a skewed angle, and serve to receive fixation pins or other means for stabilizing the bone cutting guide 20 across a targeted anatomy and/or positioning a bone or bones.

Additionally, the bone cutting guide 20 can have a secondary guide member 200. The secondary guide member 200 can be supported on the rails 170A and 170B. For example, the secondary guide member 200 may include slots 205A and 205B to receive the rails 170A and 170B such that the secondary guide member 200 is supported thereon. The secondary guide member 200 can also have a third guide surface 210A and a fourth guide surface 210B. The third and fourth guide surfaces 210A and 210B can be adjacent surfaces facing one another with a space defined between the third and fourth guide surfaces 210A and 210B. In the illustrated embodiments, third and fourth guide surfaces 210A and 210B are single, continuous surfaces that do not include a gap, but in other embodiments third and/or fourth guide surfaces 210A and 210B can include a gap. The third guide surface 210A defines a third plane, while the fourth guide surface 210B defines a fourth plane. As shown, the third guide surface 210A and fourth guide surface 210B can be configured such that the third plane is parallel to the fourth plane, with the space between. In further embodiments (not illustrated), the guide surfaces 210A and 210B can be configured such that the third and/or fourth planes are skewed. Further, the third and/or fourth guide surfaces may be parallel to or skewed with respect to the first and/or second guide surfaces, such that the cutting guide can be adapted to make parallel cuts or angular cuts or cut shapes (e.g. a chevron shape). In some embodiments, the secondary guide member 200 can be locked to the rails 170A and/or 170B with a locking screw, cam, pin, etc. In the embodiment shown in FIG. 3A, an aperture 214 is provided to receive a locking mechanism and/or an accessory, such as a handle.

Figure 4:
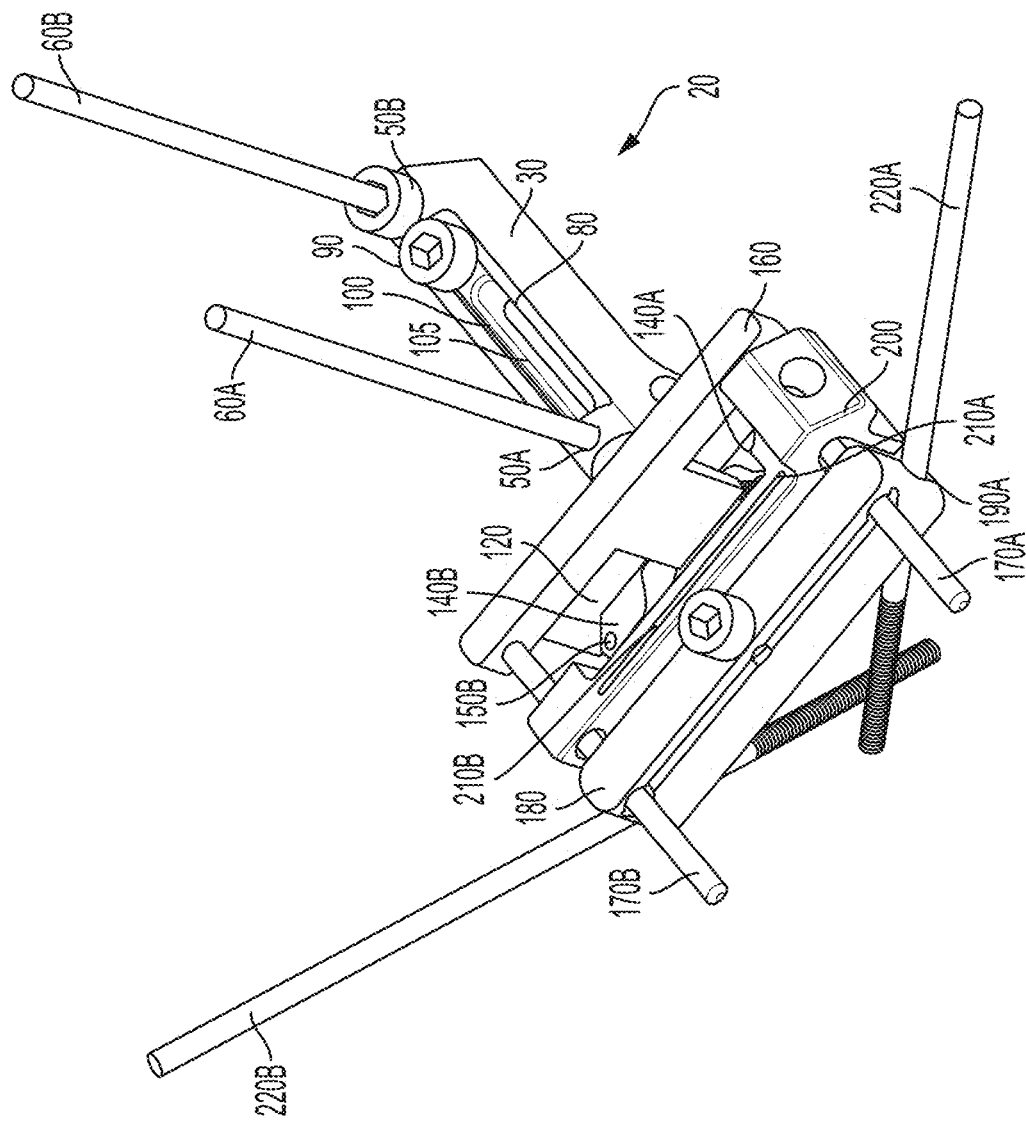
FIG. 4 is a perspective view of the bone cutting guide of FIG. 1 assembled.
Figure 5:
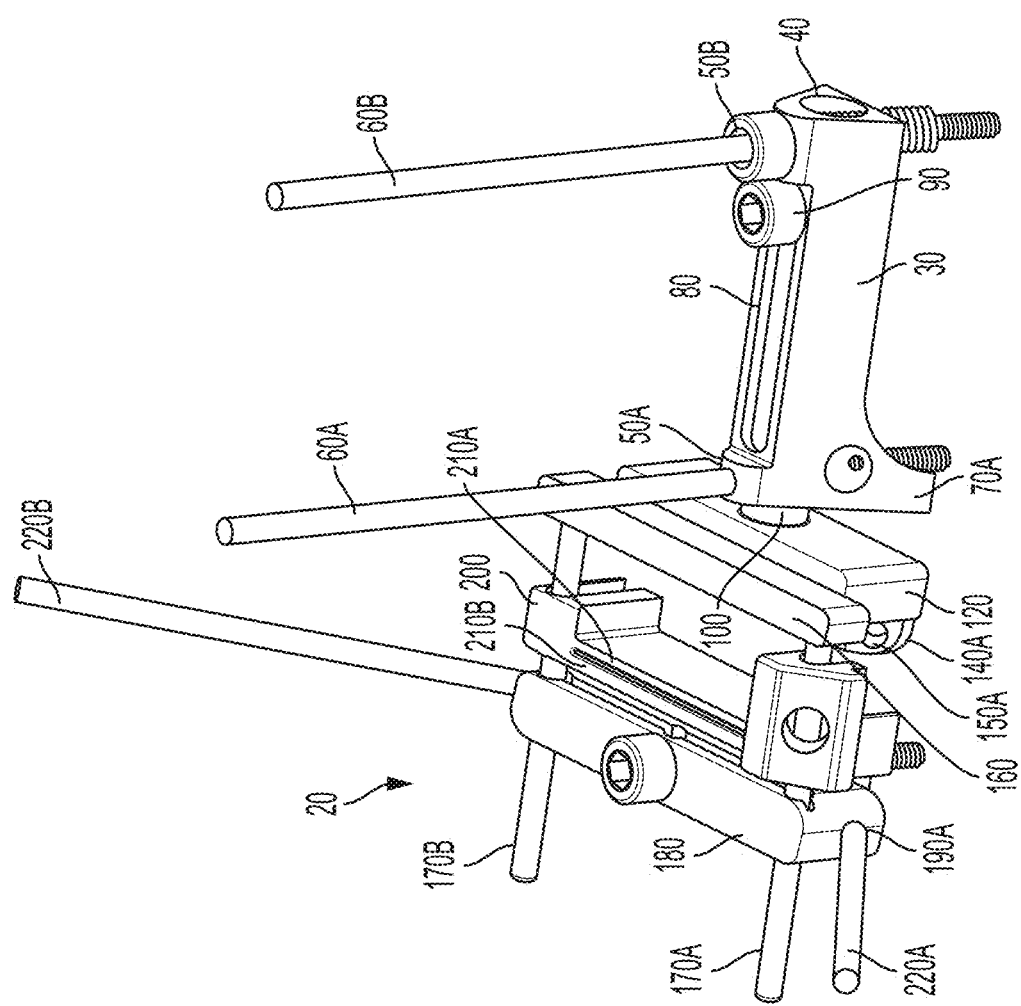
FIG. 5 is another perspective view of the bone cutting guide of FIG. 4.
Figure 6:
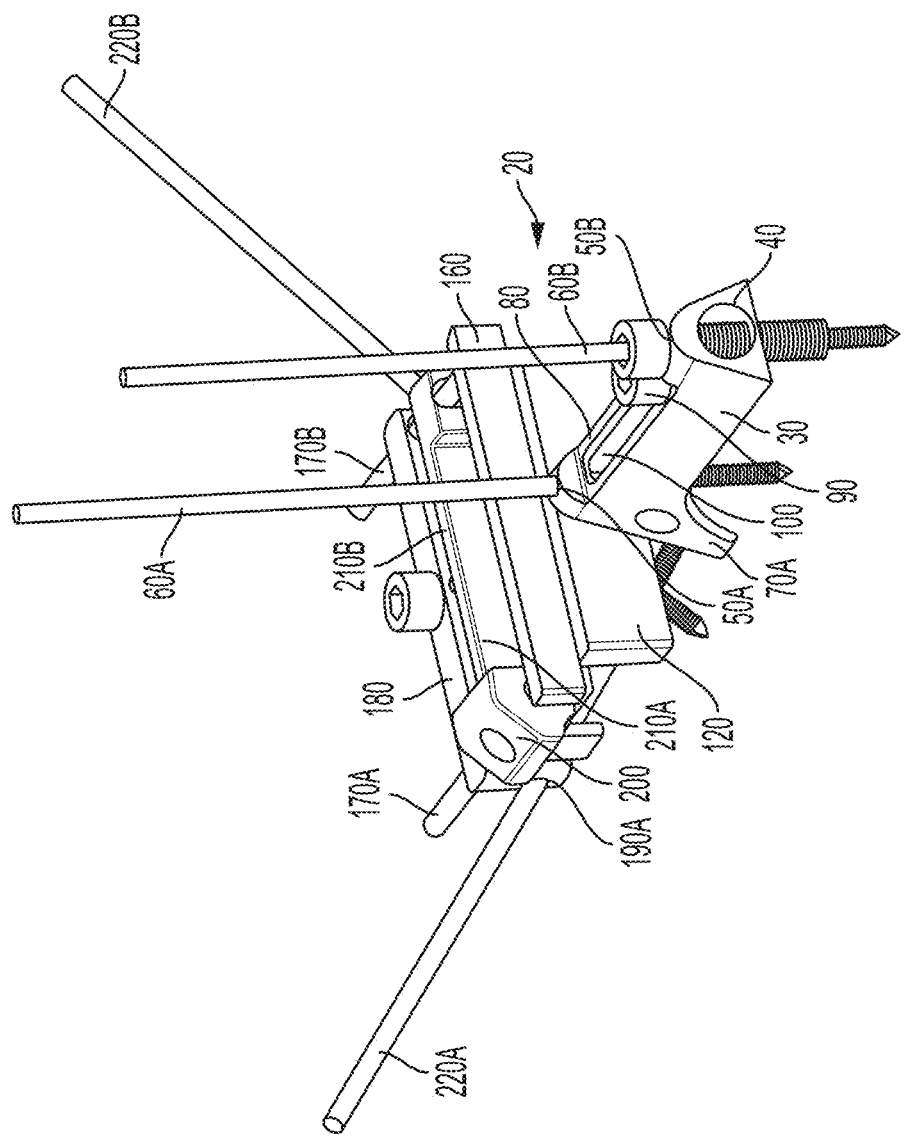
FIG. 6 is a further perspective view of the bone cutting guide of FIG. 4.

FIGS. 4-6 illustrate perspective views of the embodiment of the bone cutting guide 20, described with respect to FIGS. 1-3, as assembled. In the embodiment illustrated in FIGS. 4-6, the bridge component 160 is attached to the main guide member 120 and both the fixating structure 180 and secondary guide member 200 are supported along the rails 170A and 170B of the bridge component. In one application, the secondary guide member 200 can be supported on the rails 170A and 170B at a location along the rails 170A and 170B between the fixating structure 180 and the main guide member 120. Additionally shown in FIGS. 4-6 are fixation pins 220A and 220B received within fixation apertures 190A and 190B such that the fixation pins 220A and 220B extend through the fixating structure 180. In some applications of the bone cutting guide 20, it may be desirable to provide the fixation pins 220A and 220B at an angle other than 90 degrees relative to a top surface of the fixating structure 180 by configuring the fixation apertures 190A and 190B to extend through the fixating structure 180 at a skewed angle to guide the fixating pins 220A and 220B. Fixation pins 220A and 220B can be used, for example, for stabilizing the bone cutting guide 20 across a targeted anatomy and/or positioning a bone or bones.

Embodiments of the bone cutting guide 20 can be useful in operation for temporarily positioning a bone or bones and guiding a cutting of a bone or bones at a targeted anatomy. Bone cutting can be useful, for instance, to facilitate contact between leading edges of adjacent bones, separated by a joint, or different portions of a single bone, separated by a fracture, such as in a bone alignment and/or fusion procedure. As such, embodiments of the present invention include methods for temporarily fixing an orientation of a bone or bones, such as during a surgical procedure, and guiding cutting at desired bone locations. In the embodiments described, cuts are made to bone with respect to the cutting guide, and the bones can be positioned for an additional surgical step, such as bone plating, after the cuts have been made.

Figure 7:
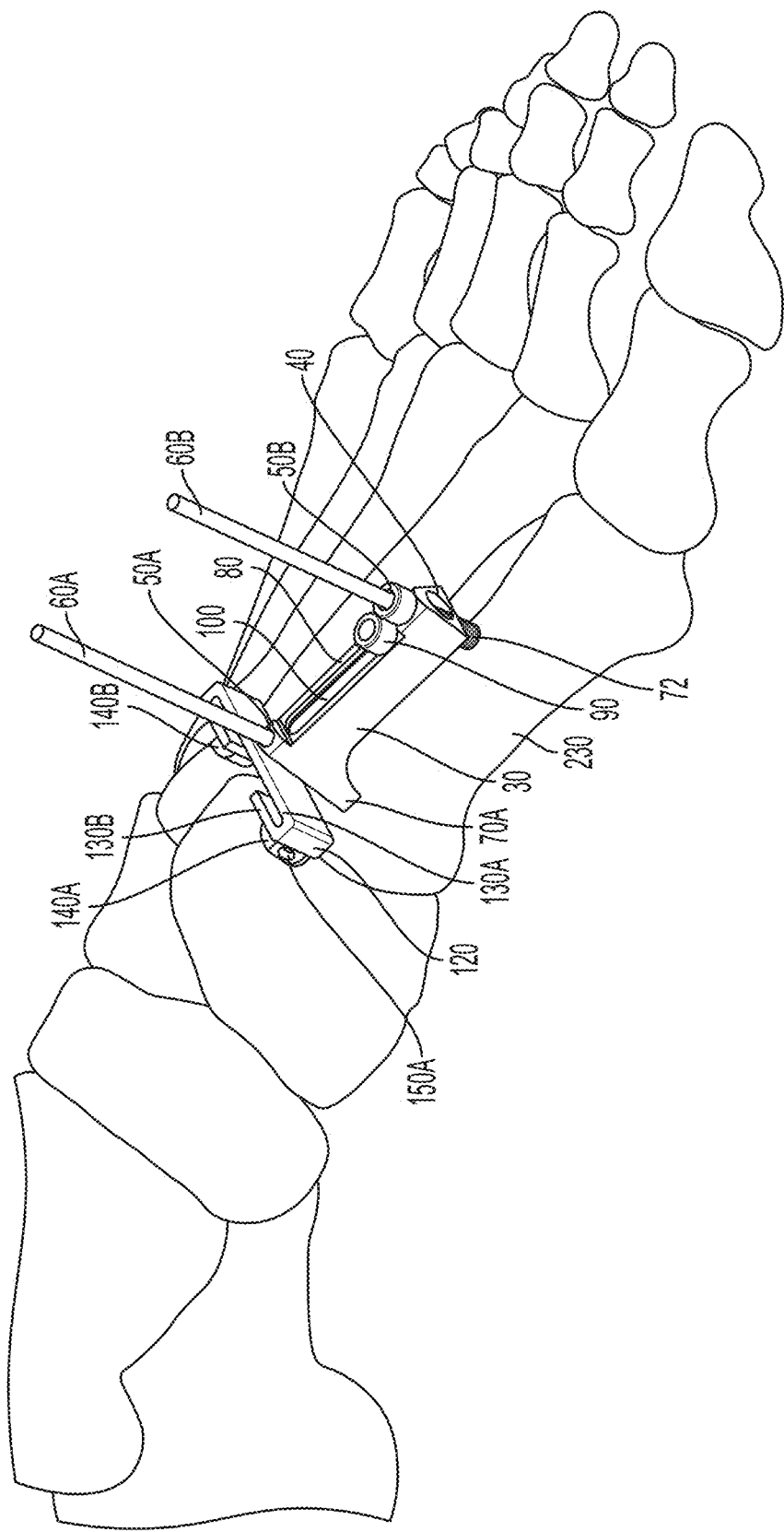
FIG. 7 is a perspective view of a bone cutting guide support fixed to a bone.
Figure 8:
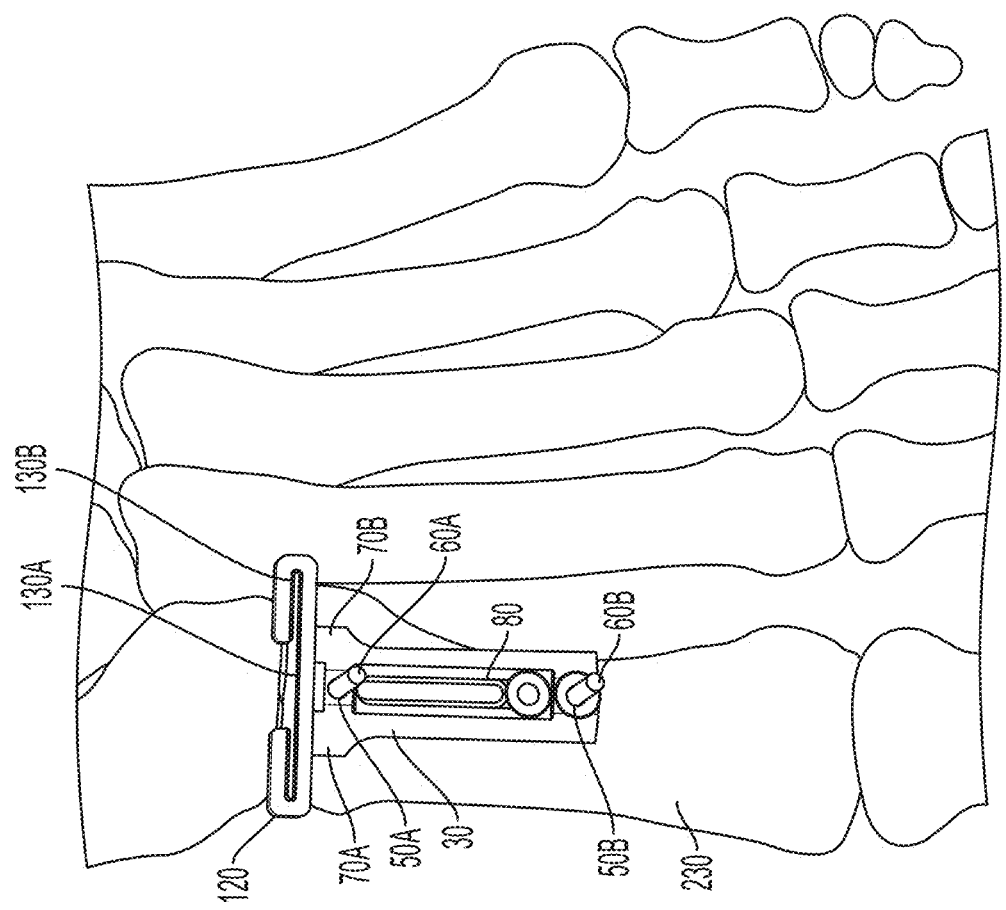
FIG. 8 is a top view of the bone cutting guide support fixed to the bone of FIG. 7.
Figure 9:
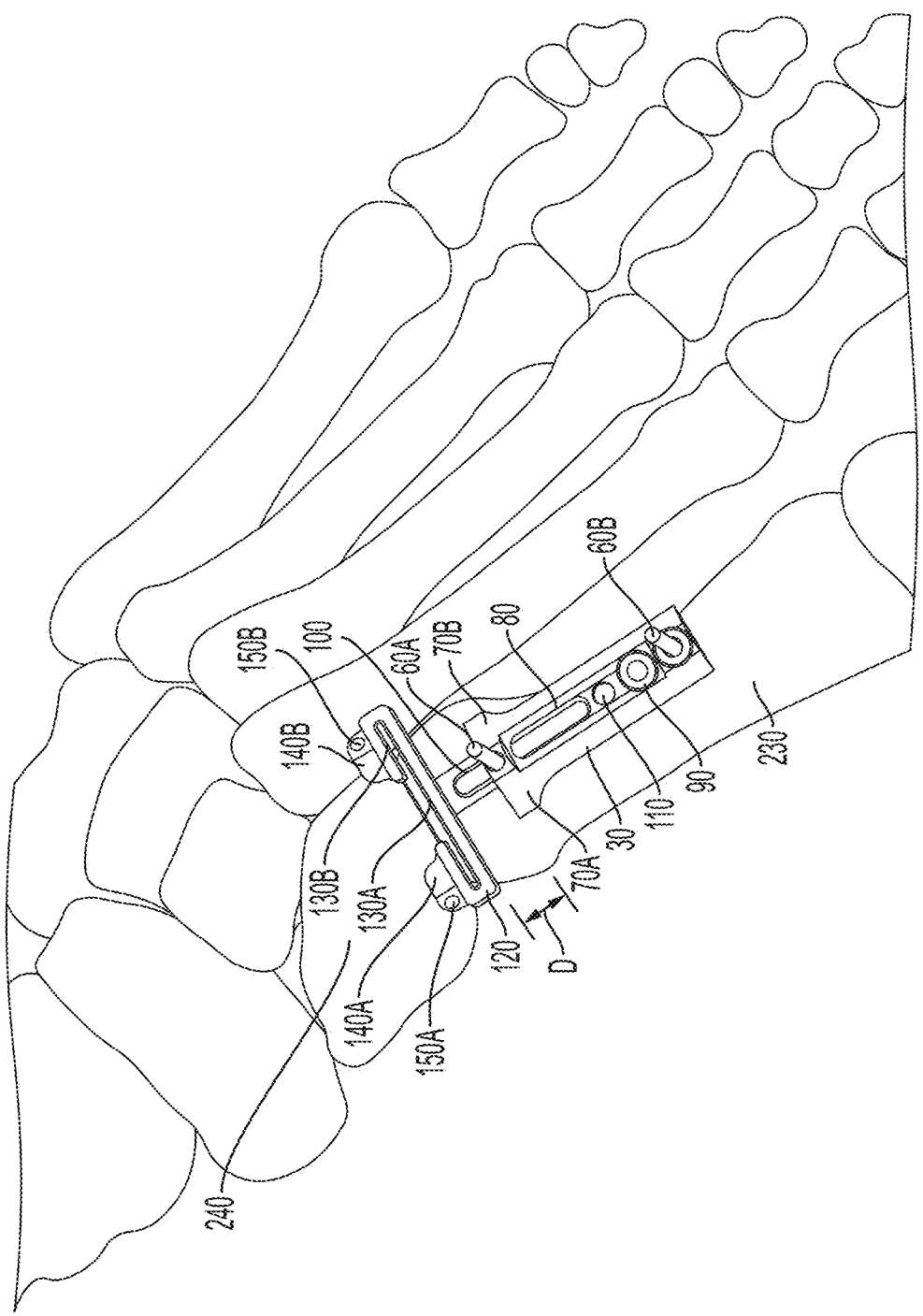
FIG. 9 is a perspective view of the bone cutting guide support fixed to the bone of FIG. 7 with a location of the main guide member adjusted.

FIGS. 7-16 illustrate steps of an embodiment of a method for temporarily positioning and cutting a bone or bones using the bone cutting guide 20. Specifically, FIGS. 7 and 8 show a perspective and top view, respectively, of the support 30 fixed to a bone 230 (e.g. a first metatarsal). The support 30 is placed on the bone 230. For embodiments of the bone cutting guide 20 that include the extensions 70A and 70B, the extensions 70A and 70B can be used to at least partially straddle the bone 230 and consequently provide both greater stability to the support 30 on the bone 230 and anatomical alignment of the support 30 on a longitudinal axis of the bone 230 (e.g., the slot 80 is generally parallel to the longitudinal axis of the bone 230). Extension member 72 can be adjusted to a desired distance from support 30. Further, in some embodiments it can be desirable to align and fix the support 30 along the longitudinal axis of the bone 230 using the fixation pins 60A and 60B. The pin 60A can be inserted through the fixation aperture 50A such that an end of the pin 60A protrudes out from the fixation aperture 50A adjacent the bone 230. The pin 60A can then be fixed to the bone 230. Similarly, the pin 60B can be inserted through fixation aperture 50B and fixed on an end to the bone 230. In this manner, the support 30 can be fixed in place to and aligned along the longitudinal axis of the bone 230.

In addition to fixing the support 30 to the bone 230, the main guide member 120 can be aligned such that the main guide member 120 is positioned at a location where a bone (e.g., the bone 230) is to be cut. In one embodiment, the main guide member 120 can be positioned at the location where a bone is to be cut by appropriately positioning and fixing the support 30, e.g., such that the support 30 is fixed to the bone 230 at a location along bone 230 that results in the main guide member 120 being positioned at the location where a bone is to be cut. In some embodiments, a joint alignment blade (not shown) is inserted though the main guide member and into a joint space to help align the main guide member in a desired position. Further, in certain embodiments, a provisional fixation pin (not shown) can be inserted through a bone of interest and into an adjacent bone (e.g., though a first metatarsal and into a second metatarsal) to provide additional stability during the procedure.

In some applications, a location of the main guide member 120 relative to the longitudinal axis of the bone 230 can be adjusted without necessitating movement of the support 30. To accomplish this, the shaft 100 at least partially within the inner cavity 40 can be translated relative to the support 30 as shown in the perspective view of FIG. 9. As shown, the main guide member 120 has been translated along the longitudinal axis of the bone 230 a distance D as a result of the shaft 100 being moved the same distance D. Once the main guide member 120 is positioned at the location to be cut, the securing component 90 can be translated along the slot 80 such that the securing component 90 is aligned with securing aperture 110. The securing component 90 can then be fixed within the securing aperture 110 such that the shaft 100 is fixed relative to the support 30.

After the main guide member 120 has been positioned at the location to be cut, a cutting member (e.g. a saw blade) can be inserted through the space defined between the first guide surface 130A and the second guide surface 130B to cut, for example, the bone 230. The guide surfaces 130A and 130B can serve to direct the cutting member to the location of the bone 230 to be cut, which in many applications can be a precise location. The break or window defined in the second guide surface 130B can assist in visualizing the portion of the bone 230 being cut.

In some embodiments, the main guide member 120 can be used to make additional cuts. In such embodiments, the securing component 90 can be loosened and the shaft 100 can be translated within the cavity to a desired position. The securing component 90 can be then be fixed within the securing aperture so the shaft is again fixed relative to the support 30. In some embodiments, fixation pins may be inserted through fixation aperture 150A and/or 150B and into the bone 230 to further stabilize the main guide member. After the main guide member 120 has been repositioned at the location to be cut, a cutting member (e.g. a saw blade) can be inserted through the space defined between the first guide surface 130A and the second guide surface 130B to cut, for example, the bone 240. The guide surfaces 130A and 130B can serve to direct the cutting member to the location of the bone 240 to be cut.

In some applications, it may be desirable to provide additional, temporary fixation of the bone 230 to allow for more accurate cutting. As best seen again in FIG. 9, blocks 140A and 140B can provide a means for additionally positioning the bone 230. Fixation pins can be inserted through the fixation aperture 150A and/or 150B and into the bone 230 to temporarily position the bone 230 and/or adjacent bone 240 for cutting. In other applications, blocks 140A and 140B may not be necessary.

Figure 10:
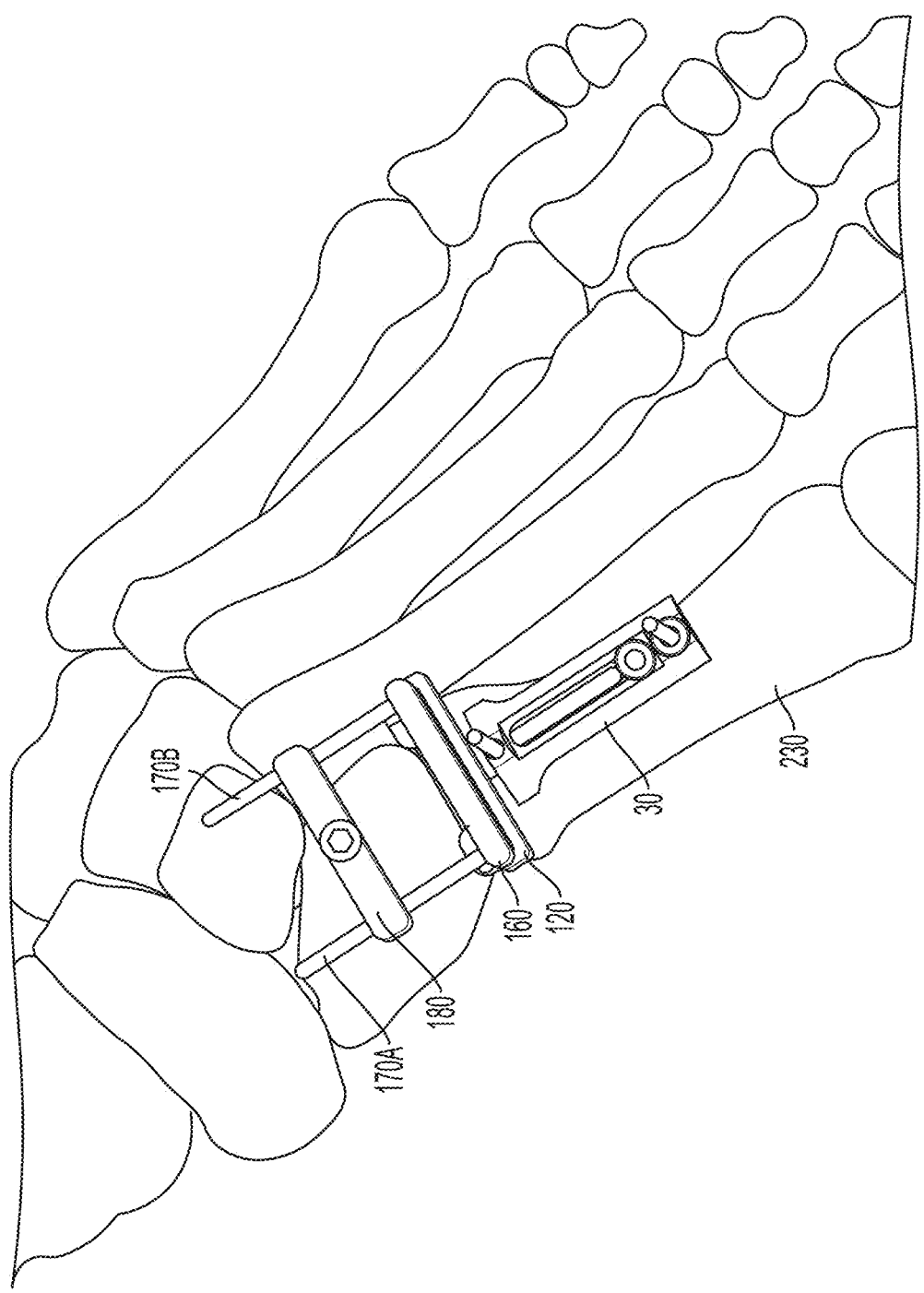
FIG. 10 is a perspective view of a bridge component attached to the main guide member of the support of FIG. 7 with a fixation structure attached to the bridge component.

As shown in the perspective view of FIG. 10, once the bone 230 has been cut the bridge component 160 can optionally be attached to the main guide member 120. In one embodiment, the bridge component 160 can have a geometry that allows the bridge component 160 to attach to the main guide member 120 between the first and second guide surfaces 130A and 130B through an interference fit, while in other embodiments the bridge component 160 can attach to the main guide member 120 by other attachment means. The rails 170A and 170B of the bridge component 160 can be arranged such that the rails 170A and 170B extend out from the bridge component 160 on a side of the bridge component 160 opposite the support 30. The rails 170A and 170B can serve to support additional components of the bone cutting guide 20.

One such component of the bone cutting guide 20 that can be supported on the rails 170A and 170B is the fixating structure 180. FIG. 10 shows the fixating structure 180 attached to the rails 170A and 170B. In one embodiment, the fixating structure 180 can have holes or slots for receiving the rails 170A and 170B such that the fixating structure 180 can translate along the rails 170A and 170B to a desired position. The fixating structure 180, for example, can also be secured to the rails 170A and 170B in a manner that prevents translation of the fixating structure 180 when desired by actuating the actuator 186.

Figure 11:
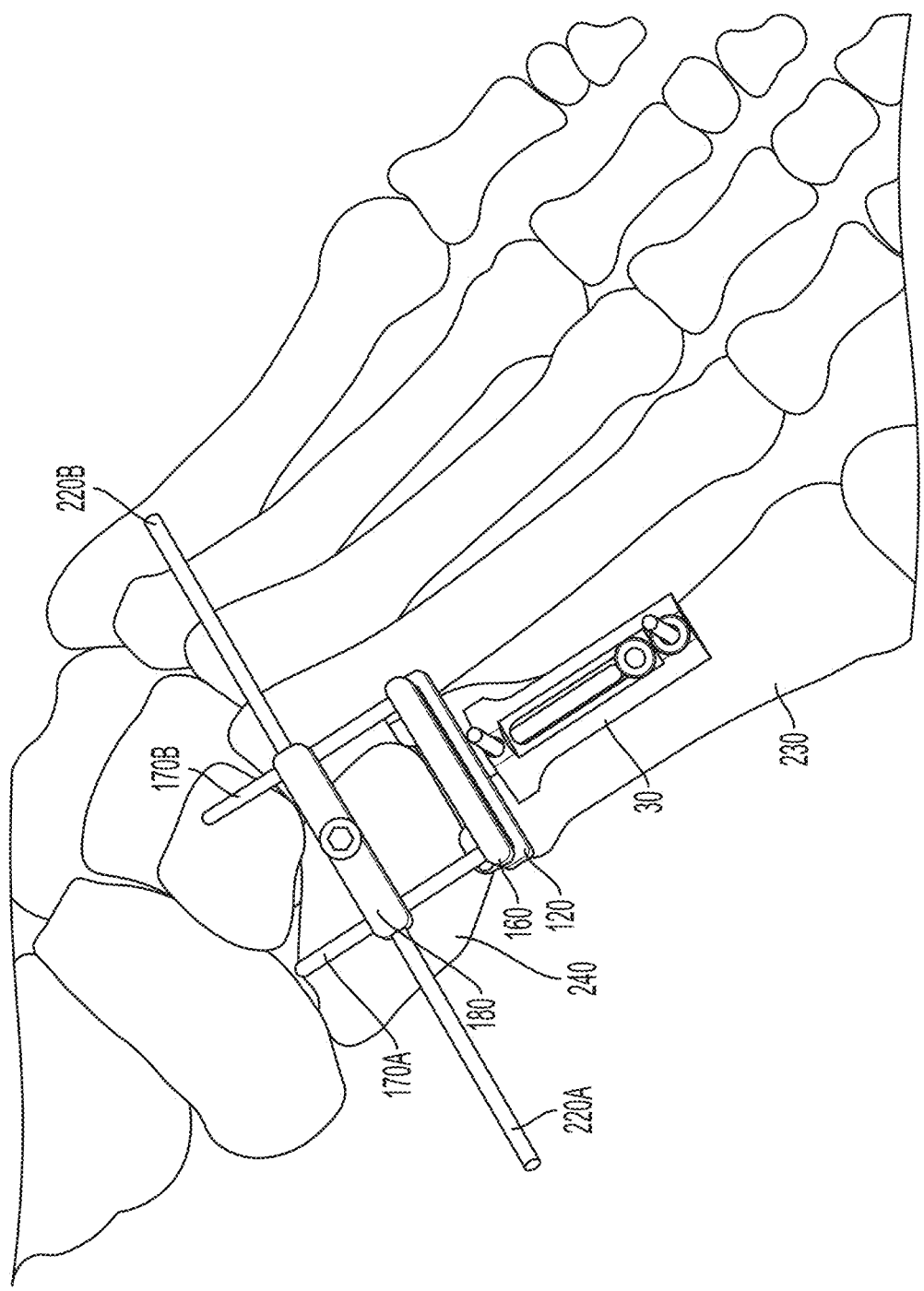
FIG. 11 is a perspective view of the fixation structure pinned across a bone.
Figure 12:
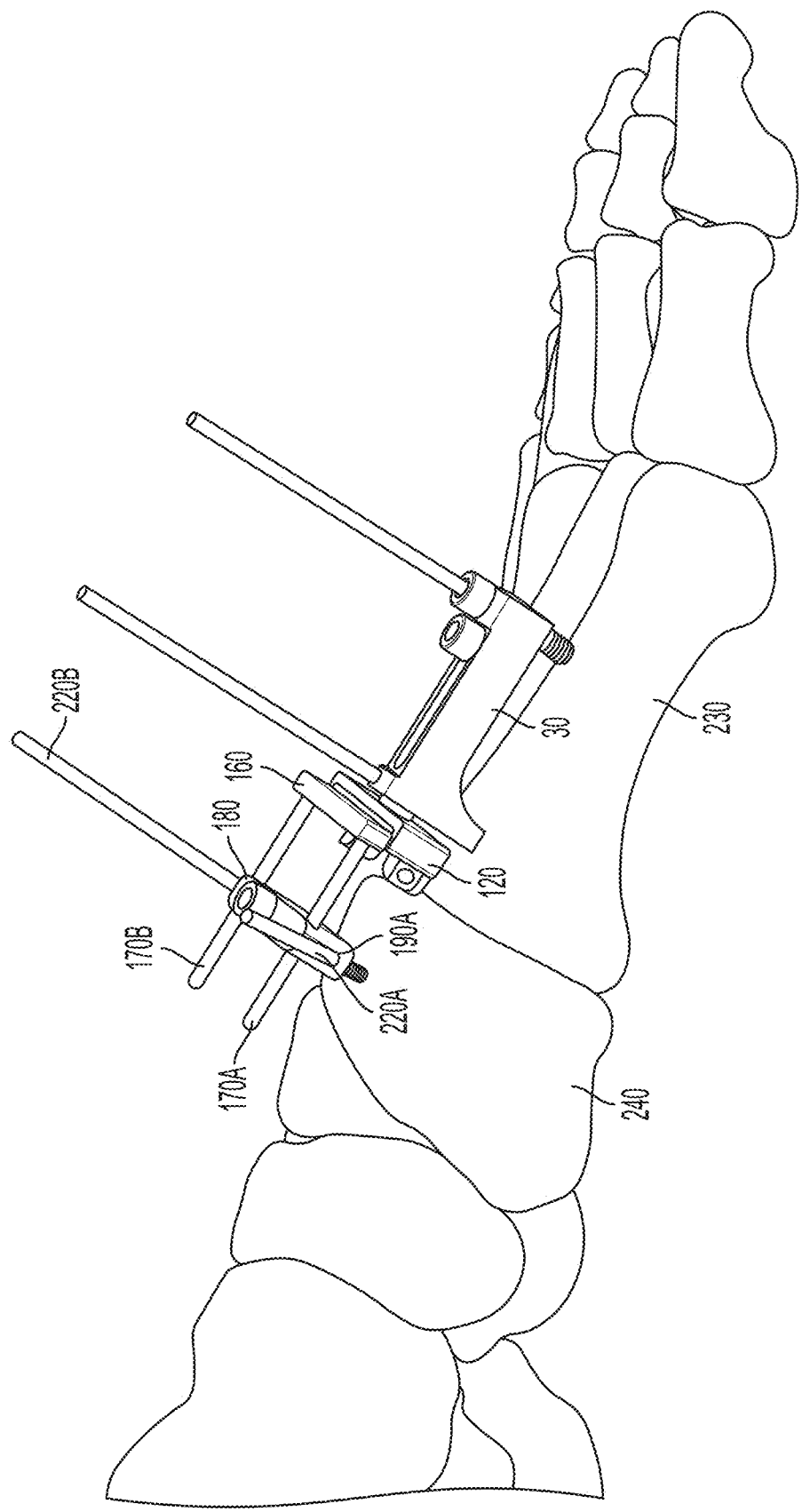
FIG. 12 is another perspective view of the pinned fixation structure of FIG. 11.

FIGS. 11 and 12 illustrate perspective views of the fixating structure 180 with the fixation pins 220A and 220B received through the fixation apertures 190A and 190B (190 B is shown in, e.g., FIG. 2). Fixation apertures 190A and 190B can be on opposite ends of the fixating structure 180 as shown. Fixation pins 220A and 220B can be fixed to a bone 240 (e.g. a first cuneiform as illustrated) to provide stability for the bone cutting guide 20 and/or to position the bone 240. After the pins 220A and 220B are set, the fixating structure 180 can be translated with respect to the rails 170A and 170B and the support 30 to a desired position to compress or expand the space between the bones 230 and 240 as needed. The position of the bones can be locked by securing the fixating structure 180 against the rails 170A and 170B. In other embodiments, such compression or expansion can be achieved by moving the shaft 100 relative to the support 30 and reengaging the securing component 90 at the new desired position.

Figure 13:
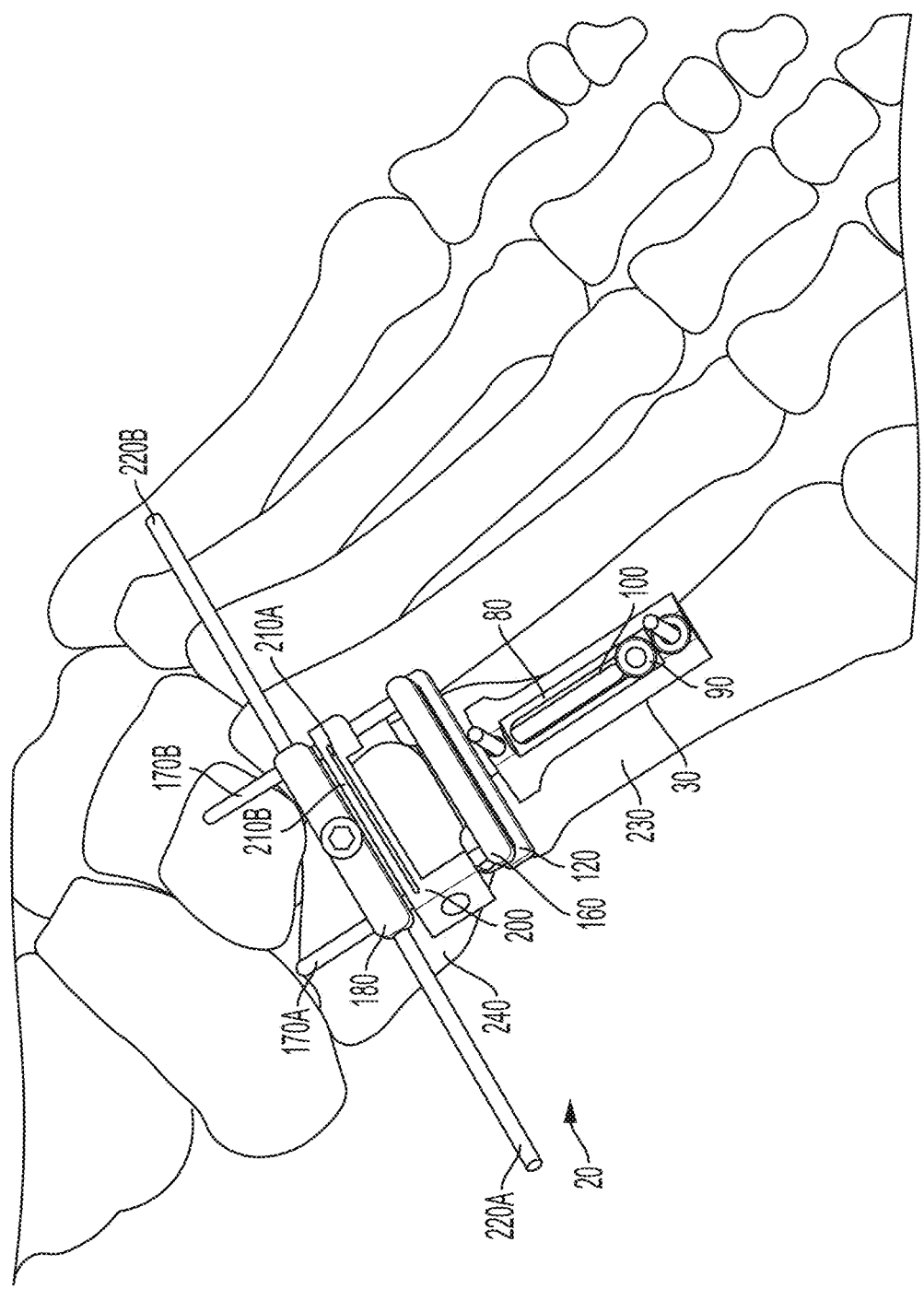
FIG. 13 is a perspective view of the assembled bone cutting guide fixed to bones.
Figure 14:
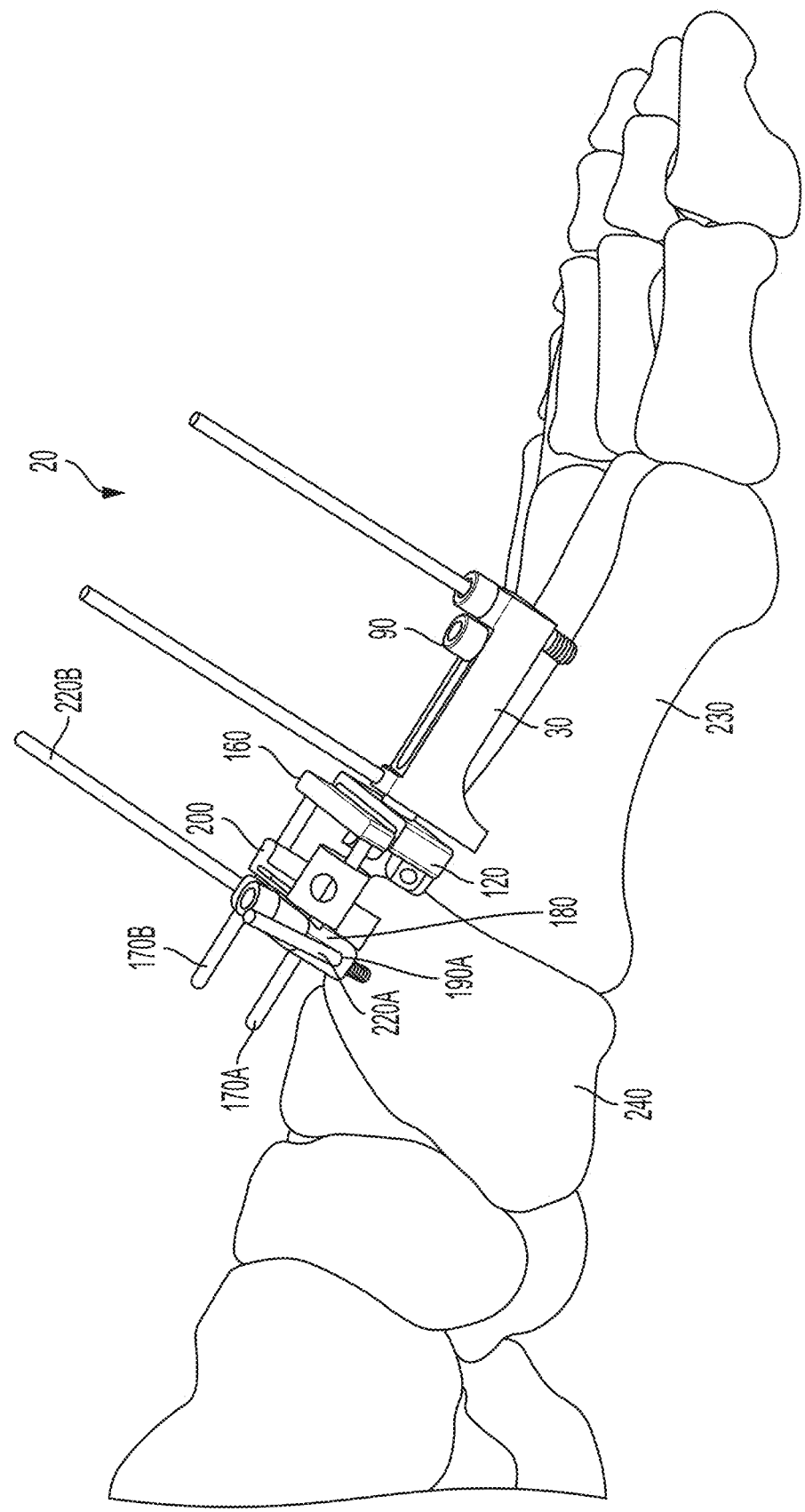
FIG. 14 is a further perspective view of the assembled bone cutting guide of FIG. 13.

FIGS. 13 and 14 show perspective views of the bone cutting guide 20 assembled to include the secondary guide member 200. The secondary guide member 200 can be supported on the rails 170A and 170B. In one embodiment, the slots 205A and 205B of the secondary guide member 200 can receive the rails 170A and 170B such that the secondary guide member 200 can translate along the rails 170A and 170B to a desired position. As illustrated, the secondary guide member 200 can be located along the rails 170A and 170B between the fixating structure 180 and the bridge component 160.

The secondary guide member 200 can be positioned at a location where a second bone cut is to be made. A cutting member (e.g. a saw blade) can be inserted through the space defined between the third and fourth guide surfaces 210A and 210B to cut, for example, the bone 240. The guide surfaces 210A and 210B can serve to direct the cutting member to the location of the bone 240 to be cut, which in many applications can be a precise location. As illustrated, the cut made using the secondary guide member 200 (e.g. to bone 240) will be a cut that is generally parallel to the cut made using the main guide member 120. However, in other embodiments components of the bone cutting guide 20 (e.g. rails 170A and 170B) can be configured such that the cut made using the secondary guide member 200 is an angular cut (i.e. not parallel) relative to the cut made using the main guide member 120.

Figure 15:
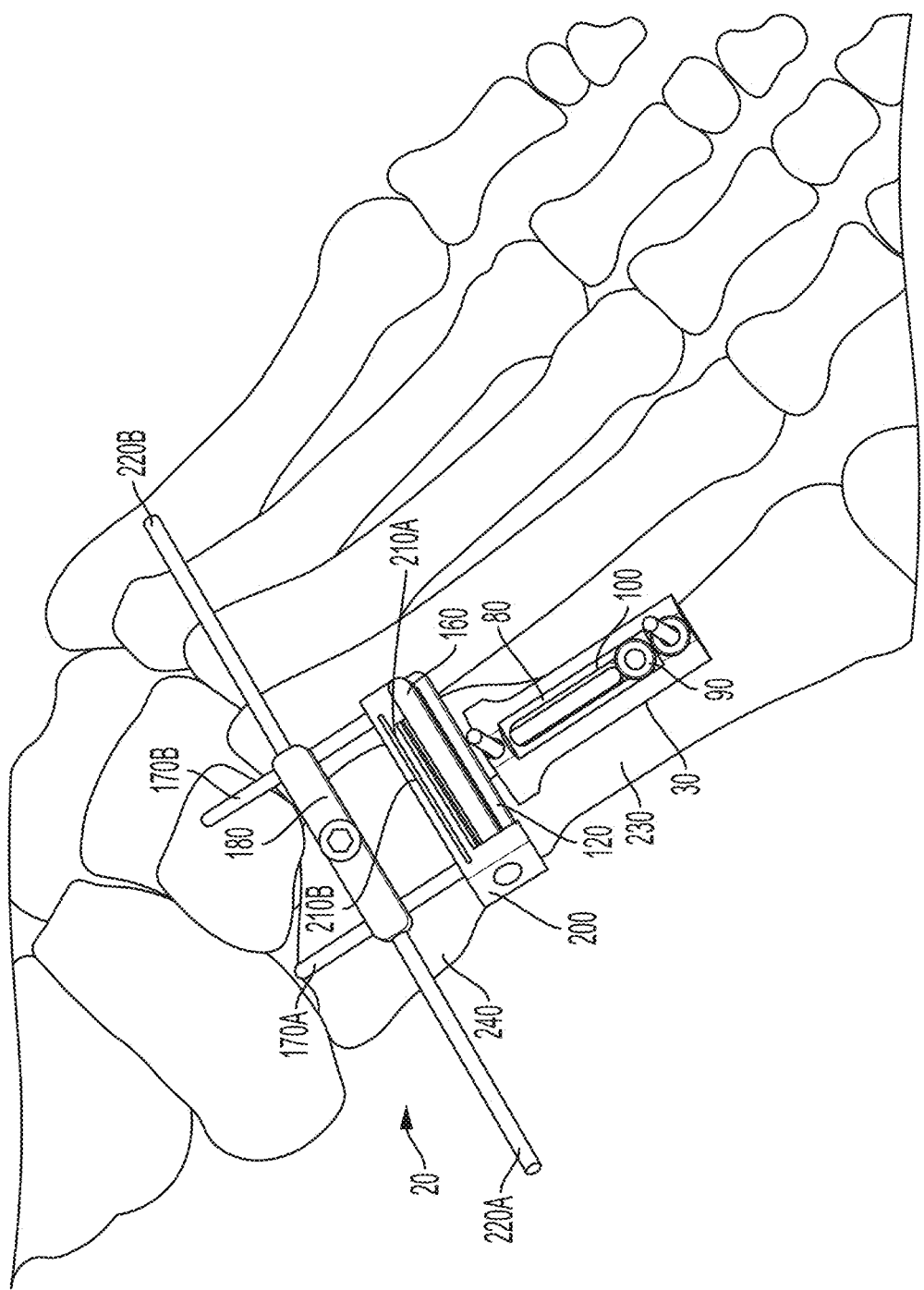
FIG. 15 shows a perspective view of the assembled bone cutting guide of FIG. 13 with a secondary guide member translated along rails of the bridge component.
Figure 16:
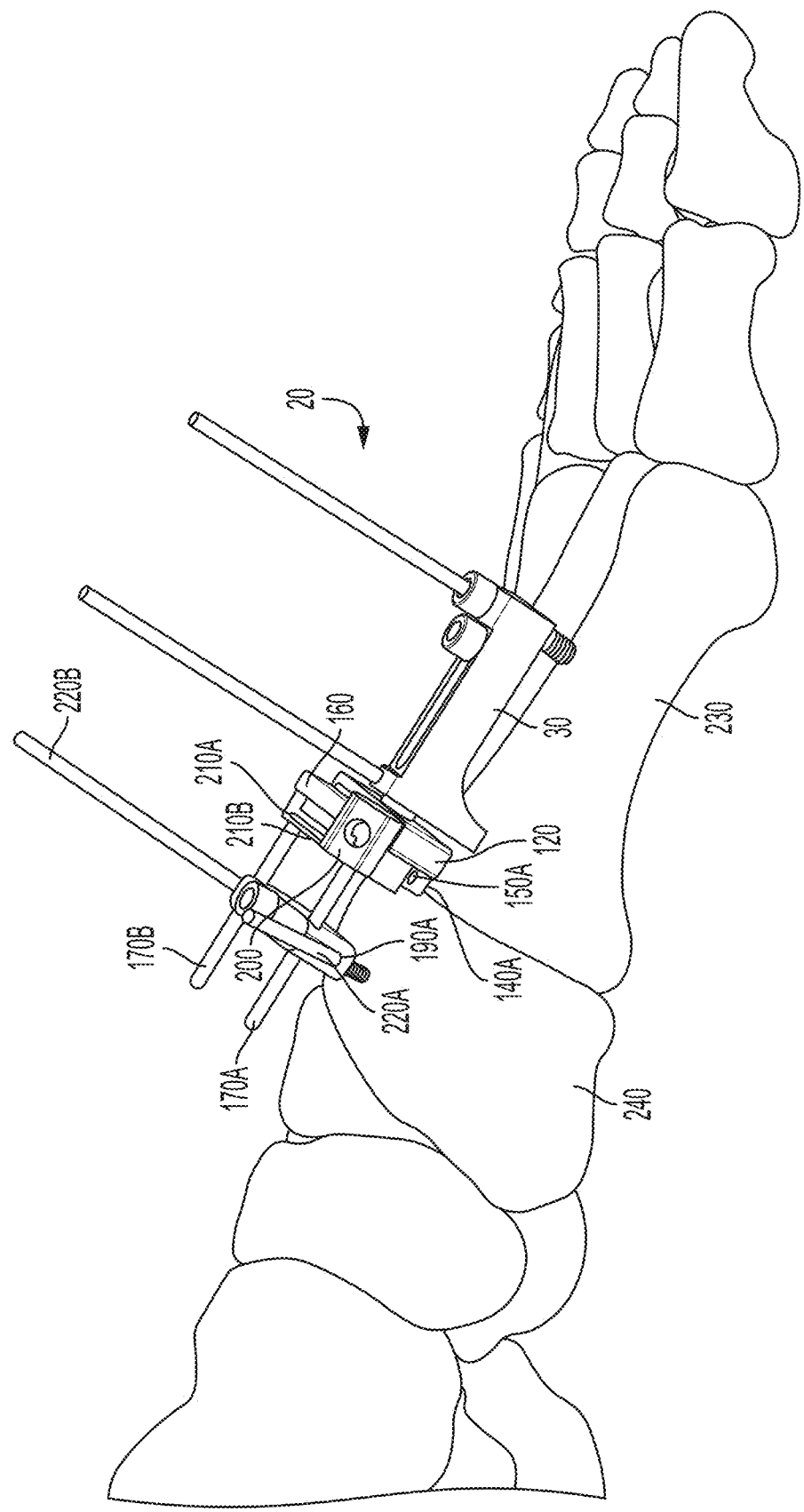
FIG. 16 is an additional perspective view of the assembled bone cutting guide of FIG. 15.

FIGS. 15 and 16 illustrate the bone cutting guide 20 as described previously, with the secondary guide member 200 translated along the rails 170A and 170B. The secondary guide member 200 can be translated along the rails 170A and 170B to precisely locate the secondary guide member 200 at the location to be cut (e.g. on bone 240). In the embodiment illustrated, the secondary guide member 200 can be shaped such that a portion of the secondary guide member 200 can overlap, or sit on top of, the bridge component 160. Such a configuration can be useful, for example, where the second cut made using the secondary guide member 200 is desired to be close to the first cut made using the main guide member 120 (e.g. portions of bones 230 and 240 interfacing at a joint).

When the bone 230 and/or bone 240 have been cut and positioned as desired, the bone cutting guide 20 can be removed. In some embodiments, the cutting guide 20 is temporarily removed from the fixation pins and cut bone is removed from the area. In certain embodiments, an autograft or other compound is delivered to the area of the bone cuts. Optionally, the guide may then be reset on the bones over the fixation pins and the shaft 100 can be translated within the cavity to adjust the relative position of the bones (e.g., to compress them together). The securing component 90 can be then be fixed within the securing aperture so the shaft is again fixed relative to the support 30. A bone plate may optionally be applied across the joint while the bones are held in the longitudinally fixed position by the cutting guide. After the plate is applied, the bone cutting guide and the fixation pins may be removed. Removing the bone cutting guide 20 can include removing all fixation pins and the support, and, in some embodiments, can include removing the bridge component, along with the fixation structure and secondary guide member 200. In certain embodiments, a second bone plate may optionally be applied across the joint. In a specific embodiment, the two bone plates are applied about 90 degrees from each other around the circumferences of the bones (e.g., at a dorsal side and a medial side).

Thus, embodiments of the invention are disclosed. Although the present invention has been described with reference to certain disclosed embodiments, the disclosed embodiments are presented for purposes of illustration, and not limitation, and other embodiments of the invention are possible. One skilled in the art will appreciate that various changes, adaptations, and modifications may be made without departing from the spirit of the invention.

The invention claimed is:

1. A method of correcting an alignment between bones of a foot, the method comprising:
    positioning a first cutting slot of a bone cutting guide over a metatarsal;
    inserting a cutting member through the first cutting slot to remove a portion of the metatarsal;
    adjusting an alignment of the metatarsal relative to a cuneiform separated from the metatarsal by a joint to establish a moved position of the metatarsal;
    positioning a second cutting slot of the bone cutting guide over the cuneiform;
    inserting the cutting member through the second cutting slot to remove a portion of the cuneiform; and
    causing the metatarsal to fuse to the cuneiform in the moved position.

2. The method of claim 1, wherein the bone cutting guide comprises a fixation aperture positioned distally of the first cutting slot, and further comprising inserting a fixation pin through the fixation aperture and into the metatarsal prior to inserting the cutting member through the first cutting slot.

3. The method of claim 1, wherein the bone cutting guide comprises a fixation aperture positioned proximally of the second cutting slot, and further comprising inserting a fixation pin through the fixation aperture and into the cuneiform prior to inserting the cutting member through the second cutting slot.

4. The method of claim 1, wherein the second cutting slot is parallel to the first cutting slot, such that inserting the cutting member through the first cutting slot and inserting the cutting member through the second cutting slot results in a cut end of the metatarsal being parallel to a cut end of the cuneiform.

5. The method of claim 1, wherein the second cutting slot is angled relative to the first cutting slot, such that inserting the cutting member through the first cutting slot and inserting the cutting member through the second cutting slot results in a cut end of the metatarsal being angled relative to a cut end of the cuneiform.

6. The method of claim 1, wherein the cutting member is a saw blade.

7. The method of claim 1, wherein positioning the first cutting slot over the metatarsal comprises positioning an alignment window defined by the bone cutting guide over the joint.

8. The method of claim 1, further comprising inserting a joint alignment blade through the bone cutting guide and into the joint to align the bone cutting guide.

9. The method of claim 1, wherein inserting the cutting member through the first cutting slot and inserting the cutting member through the second cutting slot comprises inserting the cutting member through the first cutting slot to remove the portion of the metatarsal prior to inserting the cutting member through the second cutting slot to remove the portion of the cuneiform.

10. The method of claim 1, wherein inserting the cutting member through the first cutting slot and inserting the cutting member through the second cutting slot comprises inserting the cutting member through the first cutting slot to remove the portion of the metatarsal after inserting the cutting member through the second cutting slot to remove the portion of the cuneiform.

11. The method of claim 1, wherein the bone cutting guide comprises:
   a first guide surface defining a first plane and a second guide surface defining a second plane, with the first cutting slot being provided between the first plane and the second plane, and
   a third guide surface defining a third plane and a fourth guide surface defining a fourth plane, with the second cutting slot being provided between the third plane and the fourth plane.

12. The method of claim 1, wherein positioning the first cutting slot over the metatarsal and positioning the second cutting slot over the cuneiform comprises positioning the bone cutting guide on a dorsal side of the metatarsal and the cuneiform.

13. The method of claim 1, wherein causing the metatarsal to fuse to the cuneiform in the moved position comprises delivering a compound to an area between a cut end of the metatarsal and a cut end of the cuneiform.

14. The method of claim 1, wherein causing the metatarsal to fuse to the cuneiform in the moved position comprises applying a bone plate across the joint.

15. The method of claim 14, wherein applying the bone plate comprises applying the bone plate while the metatarsal and cuneiform are held in the moved position by the bone cutting guide.

16. The method of claim 14, wherein the bone plate comprises a first bone plate, and further comprising applying a second bone plate across the joint.

17. The method of claim 16, wherein applying the first bone plate comprises applying the first bone plate on a dorsal side of the metatarsal and cuneiform, and applying the second bone plate comprises applying the second bone plate on a medial side of the metatarsal and cuneiform.

18. The method of claim 1, further comprising translating the second cutting slot perpendicularly relative to the first cutting slot to adjust a separation distance between the first cutting slot and the second cutting slot.

19. The method of claim 1, wherein causing the metatarsal to fuse to the cuneiform in the moved position comprises compressing the metatarsal and the cuneiform together.

20. The method of claim 1, wherein the metatarsal is a first metatarsal and the cuneiform is a first cuneiform.

\* \* \* \* \*

UNITED STATES PATENT AND TRADEMARK OFFICE
CERTIFICATE OF CORRECTION

PATENT NO. : 10,561,426 B1
APPLICATION NO. : 16/593153
DATED : February 18, 2020
INVENTOR(S) : Paul Dayton et al.

Page 1 of 1

It is certified that error appears in the above-identified patent and that said Letters Patent is hereby corrected as shown below:

In the Specification

In Column 4, Line 15, delete "AB" and insert -- A/B --, therefor.

Signed and Sealed this
Twenty-eighth Day of April, 2020

Andrei Iancu
*Director of the United States Patent and Trademark Office*